(12) United States Patent
Haning et al.

(10) Patent No.: US 6,777,442 B2
(45) Date of Patent: Aug. 17, 2004

(54) DIPHENYL DERIVATIVES

(75) Inventors: Helmut Haning, Milford, CT (US); Michael Woltering, Wuppertal (DE); Gunter Schmidt, Wuppertal (DE); Christiane Faeste, Haan (DE); Hilmar Bischoff, Wuppertal (DE); Axel Kretschmer, Wuppertal (DE); Verena Vöhringer, Wuppertal (DE); Peter Ellinghaus, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/082,022

(22) Filed: Feb. 26, 2002

(65) Prior Publication Data

US 2003/0105078 A1 Jun. 5, 2003

(30) Foreign Application Priority Data

Mar. 12, 2001 (DE) .......................... 101 11 651
Jun. 27, 2001 (DE) .......................... 101 30 835

(51) Int. Cl.$^7$ ..................... C07C 233/05; A61K 31/24; A61P 25/25; A61P 35/00; A61P 3/04
(52) U.S. Cl. ..................... 514/532; 514/570; 514/571; 514/618; 514/619; 514/620; 514/621; 514/622; 514/563; 514/545; 564/162; 564/163; 564/169; 564/170; 564/171; 560/11; 560/17; 560/45; 562/460; 562/429; 562/431
(58) Field of Search .............................. 560/45, 11, 17; 562/460, 429, 431; 564/162, 163, 169, 170, 171; 514/570, 571, 563, 618, 619, 620, 621, 622, 532, 545

(56) References Cited

FOREIGN PATENT DOCUMENTS

| EP | 0188351 | 7/1986 |
|---|---|---|
| EP | 0580550 | 1/1994 |
| WO | 9857919 | 12/1998 |
| WO | 9926966 | 6/1999 |
| WO | 9900353 | 7/1999 |
| WO | WO 00/07972 | * 2/2000 |
| WO | 0039077 | 6/2000 |
| WO | 0051971 | 9/2000 |
| WO | 0058279 | 10/2000 |
| WO | 0072810 | 12/2000 |
| WO | 0073265 | 12/2000 |

OTHER PUBLICATIONS

Yokoyama, N., Walker, G., Main, A., Stanton, J., Morrissey, M., Boehm, C., Engle, A., Neubert, A., Wasvary, J., Stephan, Z., Steele, R., Synthesis and Structure—Activity Relationships of Oxamic Acid and Acetic Acid Derivatives Related to L–Thyronine, J. Med. Chem., 38:695–707 (1995).

* cited by examiner

Primary Examiner—Mark L Berch
Assistant Examiner—Kahsay Habte
(74) Attorney, Agent, or Firm—Susan M. Pellegrino

(57) ABSTRACT

The present invention relates to compounds of the general formula (I)

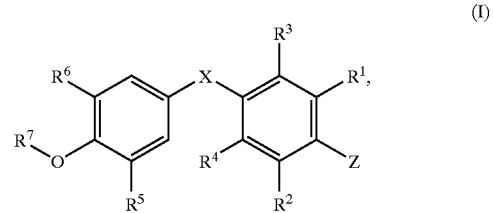

in which X represents O, S, SO, SO$_2$, CH$_2$, CHF, CF$_2$ or NR$^8$, and Z represents a group of the formula

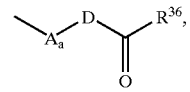

in which A represents O or S, the subscript "a" is 0 or 1, group D represents a straight-chain (C$_1$–C$_4$)-alkylene group, and R$^{36}$ represents OR$^{37}$ or NR$^{38}$R$^{39}$. It also relates to processes for preparation of such compounds and to their use in medicaments for the treatment of depression, goiter, cancer of the thyroid gland, arteriosclerosis, hypercholesterolaemia, dyslipidaemia, obesity, cardiac insufficiency, pulmonary emphysema, pain, migraine, Alzheimer's disease, osteoporosis, cardiac arrhythmias, hypothyroidism, skin disorders or diabetes.

12 Claims, No Drawings

DIPHENYL DERIVATIVES

The invention relates to novel diphenyl derivatives, to processes for their preparation and to their use in medicaments.

EP-A-580 550 describes oxamic acid derivatives having cholesterol-lowering properties in mammals. The pharmacological property that is emphasized is the reduction of plasma cholesterol, in particular of LDL cholesterol. Cholesterol-lowering actions are also described in EP-A-188 351 for certain diphenyl ethers having thyroid-hormone-like actions.

Diphenyl ethers as thyroid receptor ligands are also disclosed in WO 99/00353 and WO 00/39077. Further diphenyl derivatives having thyroid-hormone-like properties are described in WO 98/57919, WO 99/26966 and WO 00/58279. Certain diphenyl sulphones are claimed in WO 00/72810 and WO 00/73265 for treating hair loss.

It is an object of the present invention to provide novel compounds having improved, in particular pharmaceutical, actions.

It has now been found that compounds of the general formula (I)

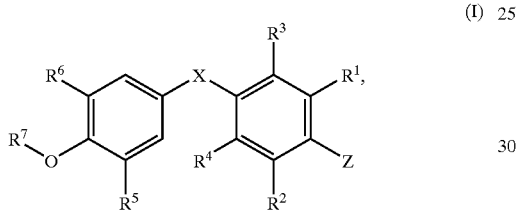

in which
X represents O, S, SO, $SO_2$, $CH_2$, CHF, $CF_2$ or represents $NR^8$ in which $R^8$ represents hydrogen or $(C_1-C_4)$-alkyl,
$R^1$ and $R^2$ are identical or different and represent hydrogen or $(C_1-C_4)$-alkyl,
$R^3$ and $R^4$ are identical or different and represent hydrogen, halogen, cyano, $(C_1-C_6)$-alkyl, $CF_3$, $CHF_2$, $CH_2F$, vinyl or $(C_3-C_7)$-cycloalkyl, where at least one of the two substituents is not hydrogen,
$R^5$ represents hydrogen, $(C_1-C_4)$-alkyl or halogen,
$R^6$ represents a group of the formula —S—$R^9$, —S(O)$_n$—$R^{10}$, —$NR^{11}$—C(O)—$R^{12}$, —$CH_2$—$R^{13}$ or —M—$R^{14}$, in which
$R^9$ represents $(C_1-C_{10})$-alkyl, $(C_3-C_8)$-cycloalkyl, $(C_2-C_6)$-alkenyl, $(C_6-C_{10})$-aryl, $(C_6-C_{10})$-arylmethyl or represents a saturated, partially unsaturated or aromatic 5- to 10-membered heterocycle having up to four identical or different heteroatoms from the group consisting of N, O and S, where the abovementioned radicals are optionally substituted by one, two or three identical or different substituents selected from the group consisting of halogen, hydroxyl, oxo, cyano, $(C_1-C_6)$-alkyl, $(C_1-C_6)$-alkoxy, carboxyl and $(C_1-C_4)$-alkoxycarbonyl,
n represents the number 1 or 2,
$R^{10}$ represents $OR^{15}$, $NR^{16}R^{17}$, $(C_1-C_{10})$-alkyl, $(C_3-C_8)$-cycloalkyl, $(C_2-C_6)$-alkenyl, $(C_6-C_{10})$-aryl, $(C_6-C_{10})$-arylmethyl or represents a saturated, partially unsaturated or aromatic 5- to 10-membered heterocycle having up to four identical or different heteroatoms from the group consisting of N, O and S, where the abovementioned radicals are optionally substituted by one, two or three identical or different substituents selected from the group consisting of halogen, hydroxyl, oxo, cyano, nitro, amino, $NR^{18}R^{19}$, trifluoromethyl, $(C_1-C_6)$-alkyl, optionally $R^{20}$-substituted $(C_1-C_6)$-alkoxy, $(C_3-C_8)$-cycloalkyl, $(C_6-C_{10})$-aryl, which for its part is optionally substituted by halogen, $(C_1-C_4)$-alkyl, $(C_1-C_4)$-alkoxy, trifluoromethyl, nitro or cyano, —O—C(O)—$R^{21}$, —C(O)—$OR^{22}$, —C(O)—$N^{23}R^{24}$, —$SO_2$—$NR^{25}R^{26}$, —NH—C(O)—$R^{27}$ and —NH—C(O)—$OR^{28}$, where
$R^{15}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and each represents hydrogen, phenyl, benzyl, $(C_1-C_6)$-alkyl or $(C_3-C_8)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or by phenyl which for its part is optionally substituted by halogen or hydroxyl, and
$R^{16}$ and $R^{17}$ are identical or different and independently of one another represent hydrogen, straight-chain or branched $(C_1-C_6)$-alkyl which may be mono- or polysubstituted by identical or different substituents from the group consisting of mono-$(C_1-C_6)$-alkylamino, di-$(C_1-C_6)$-alkyl amino, $(C_1-C_4)$-alkoxy, $(C_1-C_6)$-alkoxycarbonyl, carboxyl, pyridyl or $(C_6-C_{10})$-aryl, where the latter for its part is optionally substituted by halogen, trifluoromethyl, $(C_1-C_6)$-alkyl or $(C_1-C_6)$-alkoxy, represent $(C_3-C_8)$-cycloalkyl or represent a 5- to 7-membered heterocycle which contains one or two nitrogen atoms, where cycloalkyl and heterocycle are optionally substituted by $(C_1-C_4)$-alkyl, or
$R^{16}$ and $R^{17}$ together with the nitrogen atom to which they are attached form a 5- to 7-membered saturated, optionally benzo-fused heterocycle which may contain up to two further heteroatoms from the group consisting of N, O and S and which may be substituted by amino, $(C_1-C_6)$-alkyl, $(C_1-C_4)$-alkoxycarbonyl, $(C_1-C_4)$-alkoxycarbonylamino or phenyl,
$R^{11}$ represents hydrogen, straight-chain or branched $(C_1-C_6)$-alkyl which may be mono- or polysubstituted by identical or different substituents from the group consisting of mono-$(C_1-C_6)$-alkylamino, di-$(C_1-C_6)$-alkylamino, $(C_1-C_4)$-alkoxy, $(C_1-C_6)$-alkoxycarbonyl, carboxyl, pyridyl and $(C_6-C_{10})$-aryl, where the latter for its part is optionally substituted by halogen, trifluoromethyl, $(C_1-C_6)$-alkyl or $(C_1-C_6)$-alkoxy, represents $(C_3-C_8)$-cycloalkyl or represents a 5- to 7-membered heterocycle which contains one or two nitrogen atoms, where cycloalkyl and heterocycle are optionally substituted by $(C_1-C_4)$-alkyl,
$R^{12}$ represents straight-chain or branched $(C_1-C_{15})$-alkyl which may be substituted by $(C_3-C_8)$-cycloalkyl, $(C_1-C_4)$-alkoxy, phenyl, phenoxy or benzyloxy, where the aromatic radicals mentioned for their part may each be substituted up to three times by identical or different substituents from the group consisting of halogen, $(C_1-C_6)$-alkyl and $(C_1-C_4)$-alkoxy,
represents $(C_3-C_8)$-cycloalkyl which may be substituted by $(C_1-C_4)$-alkoxy or phenyl,
represents $(C_6-C_{10})$-aryl which may be substituted up to three times by identical or different substituents from the group consisting of $(C_1-C_6)$-alkyl, $(C_1-C_6)$-alkoxy, halogen, cyano, amino, trifluoromethyl and phenyl, or represents a 5- or 6-membered saturated or aromatic, optionally benzo-fused heterocycle having up to two heteroatoms from the group consisting of N, O and S, or represents a group of the formula —OR$^{29}$ or —NR$^{30}$R$^{31}$, in which R$^{29}$ represents straight-chain or branched $(C_1-C_6)$-alkyl, and R$^{30}$ and R$^{31}$ are identical or different and independently of one another represent hydrogen, straight-chain or branched $(C_1-C_{12})$-alkyl which may be substituted by aminocarbonyl, a group of the formula —NR$^{32}$R$^{33}$, 5- or 6-membered heteroaryl which contains up to 3 heteroatoms selected from the group consisting of N, O and S, or by phenyl, where phenyl is optionally substituted up to two times by identical or different substituents from the group consisting of halogen, $(C_1-C_4)$-alkyl, trifluoromethyl and $(C_1-C_4)$-alkoxy, represent $(C_3-C_8)$-cycloalkyl which may be substituted by $(C_1-C_4)$-alkyl, represent $(C_6-C_{10})$-aryl which may be substituted up to three times by identical or different substituents from the group consisting of halogen, $(C_1-C_4)$-alkyl, trifluoromethyl, $(C_1-C_4)$-alkoxy, amino, phenyl and phenoxy, or represent a 5- to 7-membered saturated or unsaturated heterocycle which contains one or two nitrogen atoms and is optionally substituted by $(C_1-C_4)$-alkyl or an oxo group, where R$^{32}$ and R$^{33}$ are identical or different and independently of one another represent hydrogen, $(C_1-C_6)$-alkyl, phenyl or $(C_6-C_{10})$-arylsulphonyl, or together with the nitrogen atom to which they are attached form a 3- to 7-membered saturated heterocycle which optionally contains up to two further heteroatoms from the group consisting of N, O and S or R$^{30}$ and R$^{31}$ together with the nitrogen atom to which they are attached form a 4- to 7-membered saturated heterocycle which may contain up to two further heteroatoms from the group consisting of N, O and S and which may be substituted by amino, $(C_1-C_6)$-alkyl, $(C_1-C_4)$-alkanoyl, aminocarbonyl, $(C_1-C_4)$-alkoxycarbonyl, $(C_1-C_4)$-alkoxycarbonylamino, phenyl or pyridyl, R$^{13}$ represents a saturated, partially unsaturated or aromatic 5- to 10-membered heterocycle having up to three identical or different heteroatoms from the group consisting of N, O and S, which is optionally substituted by one, two or three identical or different substituents selected from the group consisting of $(C_1-C_4)$-alkyl, hydroxyl, oxo, $(C_1-C_4)$-alkoxy, halogen, cyano, carboxyl and $(C_1-C_4)$-alkoxycarbonyl, with the proviso that X in this case does not represent SO or SO$_2$, or R$^{13}$ represents the group —NR$^{34}$R$^{35}$ in which R$^{34}$ and R$^{35}$ are identical or different and represent hydrogen, $(C_1-C_8)$-alkyl which may be substituted by $(C_6-C_{10})$-aryl, represent $(C_3-C_8)$-cycloalkyl, $(C_6-C_{10})$-aryl or represent 5- or 6-membered heteroaryl having up to three identical or different heteroatoms from the group consisting of N, O and S where aryl and heteroaryl for their part are in each case optionally mono- or disubstituted by identical or different substituents from the group consisting of hydroxyl, amino, cyano, halogen, trifluoromethyl, $(C_1-C_4)$-alkyl, $(C_1-C_4)$-alkoxy, carboxyl, $(C_1-C_4)$-alkoxycarbonyl and mono- and di-$(C_1-C_4)$-alkylaminocarbonyl, M represents C=O, CH(OH), CHF or CF$_2$, and R$^{14}$ has the meaning of R$^{10}$ given above, R$^7$ represents hydrogen, $(C_1-C_4)$-alkyl or $(C_1-C_4)$-alkanoyl, and Z represents a group of the formula

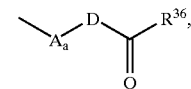

in which

A represents O or S, a represents the number 0 or 1,

D represents a straight-chain $(C_1-C_4)$-alkylene group which may be mono- or polysubstituted by identical or different substituents from the group consisting of $(C_1-C_3)$-alkyl, hydroxyl and fluorine, and R$^{36}$ represents OR$^{37}$ or NR$^{38}$R$^{39}$, in which R$^{37}$, R$^{38}$ and R$^{39}$ are identical or different and each represents hydrogen, phenyl, benzyl, $(C_1-C_6)$-alkyl or $(C_3-C_8)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or by phenyl which for its part is optionally substituted by halogen or hydroxyl, and their pharmaceutically acceptable salts, solvates, hydrates and hydrates of the salts, have pharmacological action and can be used as medicaments or for preparing medicament formulations.

Heterocycles which may be mentioned as being preferred in the definition of R$^9$, R$^{10}$ or R$^{13}$ are:

A 5- to 10-membered saturated, partially unsaturated or aromatic heterocycle having up to 4 heteroatoms from the group consisting of S, N and O, i.e. a mono- or bicyclic heterocycle which may contain one or more double bonds and is attached via a ring carbon atom or, if appropriate, via a ring nitrogen atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, azepinyl, 1,4-diazepinyl, furanyl, pyrrolyl, thienyl, thiazolyl, oxazolyl, imidazolyl, triazolyl, tetrazolyl, pyridyl, pyrimidinyl, pyrazinyl, pyridazinyl, pyrimidinonyl, pyridazinonyl, indolyl, benzo[b]thienyl, benzo[b]furyl, benzimidazolyl, indazolyl, quinolyl, isoquinolyl, naphthyridinyl, quinazolinyl.

Among this list, preference is given to: pyridyl, pyrimidinyl, pyridazinyl, pyrimidinonyl, pyridazinonyl and thienyl.

In the context of the invention, alkyl represents a straight-chain or branched alkyl radical having preferably 1 to 15, 1 to 12, 1 to 10, 1 to 8, 1 to 6, 1 to 4 or 1 to 3 carbon atoms. Preference is given to a straight-chain or branched alkyl radical having 1 to 4 carbon atoms. By way of example and by way of preference, the following radicals may be mentioned: methyl, ethyl, n-propyl, isopropyl, n-, i-, s- or t-butyl, n-pentyl and n-hexyl.

In the context of the invention, alkenyl represents a straight-chain or branched alkenyl radical having preferably 2 to 6 or 2 to 4 carbon atoms. Preference is given to a straight-chain or branched alkenyl radical having 2 to 4 carbon atoms. By way of example and by way of preference, the following radicals may be mentioned: vinyl, allyl, isopropenyl and n-but-2-en-1-yl.

In the context of the invention, an alkylene group represents a straight-chain saturated alkylene group having preferably 1 to 4, 1 to 3 or 1 or 2 carbon atoms, or represents a straight-chain unsaturated alkylene group having preferably 2 to 4 or 2 or 3 carbon atoms. By way of example and by way of preference, the following radicals may be mentioned: methylene, 1,2-ethylene, 1,3-propylene, 1,4-butylene, 1,2-vinylene and 1,3-propenylene.

In the context of the invention, aryl represents an aromatic radical having preferably 6 to 10 carbon atoms. Preferred aryl radicals are phenyl and naphthyl.

In the context of the invention, cycloalkyl represents a cycloalkyl group having preferably 3 to 8, 3 to 7 or 3 to 6 carbon atoms. By way of example and by way of preference, the following radicals may be mentioned: cyclopropyl, cyclobutyl, cyclopentyl, cyclohexyl and cycloheptyl.

In the context of the invention, alkoxy preferably represents a straight-chain or branched alkoxy radical having 1 to 6, 1 to 4 or 1 to 3 carbon atoms. Preference is given to a straight-chain or branched alkoxy radical having 1 to 3 carbon atoms. By way of example and by way of preference, the following radicals may be mentioned: methoxy, ethoxy, n-propoxy, isopropoxy, t-butoxy, n-pentoxy and n-hexoxy.

In the context of the invention, alkoxycarbonyl preferably represents a straight-chain or branched alkoxy radical having 1 to 6 or 1 to 4 carbon atoms which is attached via a carbonyl group. Preference is given to a straight-chain or branched alkoxycarbonyl radical having 1 to 4 carbon atoms. By way of example and by way of preference, the following radicals may be mentioned: methoxycarbonyl, ethoxycarbonyl, n-propoxycarbonyl, isopropoxycarbonyl and t-butoxycarbonyl.

In the context of the invention, alkanoyl preferably represents a straight-chain or branched alkyl radical having 1 to 6 or 1 to 4 carbon atoms which carries a doubly attached oxygen atom in the 1-position and is attached via the 1-position. Preference is given to a straight-chain or branched alkanoyl radical having 1 to 4 carbon atoms. By way of example and by way of preference, the following radicals may be mentioned: formyl, acetyl, propionyl, n-butyryl, i-butyryl, pivaloyl and n-hexanoyl.

In the context of the invention, alkanoyloxy preferably represents a straight-chain or branched alkyl radical having 1 to 6, 1 to 5 or 1 to 3 carbon atoms which carries a doubly attached oxygen atom in the 1-position and is attached in the 1-position via a further oxygen atom. Preference is given to a straight-chain or branched alkanoyloxy radical having 1 to 3 carbon atoms. By way of example and by way of preference, the following radicals may be mentioned: acetoxy, propionoxy, n-butyroxy, i-butyroxy, pivaloyloxy and n-hexanoyloxy.

In the context of the invention, monoalkylamino represents an amino group having a straight-chain or branched alkyl substituent which has preferably 1 to 6, 1 to 4 or 1 or 2 carbon atoms. Preference is given to a straight-chain or branched monoalkylamino radical having 1 to 4 carbon atoms. By way of example and by way of preference, the following radicals may be mentioned: methylamino, ethylamino, n-propylamino, isopropylamino, t-butylamino, n-pentylamino and n-hexylamino.

In the context of the invention, dialkylamino represents an amino group having two identical or different straight-chain or branched alkyl substituents which preferably each have 1 to 6, 1 to 4 or 1 or 2 carbon atoms. Preference is given to straight-chain or branched dialkylamino radicals having in each case 1 to 4 carbon atoms. By way of example and by way of preference, the following radicals may be mentioned: N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

In the context of the invention, mono- or dialkylaminocarbonyl represents an amino group which is attached via a carbonyl group and which has a straight-chain or branched or two identical or different straight-chain or branched alkyl substituents having preferably each 1 to 4 or 1 or 2 carbon atoms. By way of example and by way of preference, the following radicals may be mentioned: methylaminocarbonyl, ethylaminocarbonyl, isopropylaminocarbonyl, t-butylaminocarbonyl, N,N-dimethylaminocarbonyl, N,N-diethylaminocarbonyl, N-ethyl-N-methylaminocarbonyl and N-t-butyl-N-methylaminocarbonyl.

In the context of the invention, monoacylamino represents an amino group having a straight-chain or branched alkanoyl substituent which preferably has 1 to 6, 1 to 4 or 1 or 2 carbon atoms and is attached via the carbonyl group. Preference is given to a monoacylamino radical having 1 or 2 carbon atoms. By way of example and by way of preference, the following radicals may be mentioned: formamido, acetamido, propionamido, n-butyramido and pivaloylamido.

In the context of the invention, alkoxycarbonylamino represents an amino group having a straight-chain or branched alkoxycarbonyl substituent which preferably has 1 to 6 or 1 to 4 carbon atoms in the alkoxy radical and is attached via the carbonyl group. Preference is given to an alkoxycarbonylamino radical having 1 to 4 carbon atoms. By way of example and by way of preference, the following radicals may be mentioned: methoxycarbonylamino, ethoxycarbonylamino, n-propoxycarbonylamino and t-butoxycarbonylamino.

In the context of the invention, 5- or 6-membered heteroaryl having up to 3 identical or different heteroatoms from the group consisting of S, N and O preferably represents an aromatic heterocycle which is attached via a ring carbon atom of the heteroaromatic moiety, optionally also via a ring nitrogen atom of the heteroaromatic moiety. By way of example, the following radicals may be mentioned: furanyl, pyrrolyl, thienyl, thiazolyl, oxazolyl, imidazolyl, triazolyl, pyridyl, pyrimidinyl, pyridazinyl. Preference is given to pyridyl, pyrimidinyl, pyridazinyl, furyl and thiazolyl.

In the context of the invention, a 3- to 7-, 4- to 7- or 5- to 7-membered saturated or partially unsaturated heterocycle having up to 3 identical or different heteroatoms from the group consisting of S, N and O preferably represents a heterocycle which may contain one or two double bonds and which is attached via a ring carbon atom or a ring nitrogen atom. Preference is given to a 5- to 7-membered saturated heterocycle having up to 2 identical or different heteroatoms from the group consisting of S, N and O. By way of example, the following radicals may be mentioned: tetrahydrofur-2-yl, tetrahydrofur-3-yl, pyrrolidin-1-yl, pyrrolidin-2-yl, pyrrolidin-3-yl, pyrrolin-1-yl, piperidin-1-yl, piperidin4-yl, 1,2-dihydropyridin-1-yl, 1,4-dihydropyridin-1-yl, piperazin-1-yl, morpholin-4-yl, thiomorpholin4-yl, azepin-1-yl, 1,4-diazepin-1-yl. Preference is given to piperidinyl, piperazinyl, morpholinyl and pyrrolidinyl.

In the context of the invention, halogen includes fluorine, chlorine, bromine and iodine. Preference is given to fluorine, chlorine or bromine.

Depending on the substitution pattern, the compounds according to the invention can exist in stereoisomeric forms which are either like image and mirror image (enantiomers) or are not like image and mirror image (diastereomers). The invention relates both to the enantiomers or diastereomers and to their respective mixtures. The racemates, like the diastereomers, can be separated in a known manner into the stereoisomerically uniform components.

Furthermore, certain compounds can be present in tautomeric forms. This is known to the person skilled in the art, and such compounds are likewise embraced by the scope of the invention.

The compounds according to the invention can also be present as salts. In the context of the invention, preference is given to physiologically acceptable salts.

Physiologically acceptable salts can be salts of the compounds according to the invention with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Physiologically acceptable salts can also be salts of the compounds according to the invention with bases such as, for example, metal or ammonium salts. Preferred examples are alkali metal salts (for example sodium salts or potassium salts), alkaline earth metal salts (for example magnesium salts or calcium salts), and also ammonium salts derived from ammonia or organic amines, such as, for example, ethylamine, di- or triethylamine, ethyldiisopropylamine, monoethanolamine, di- or triethanolamine, dicyclohexylamine, dimethylaminoethanol, dibenzylamine, N-methylmorpholine, dihydroabietylamine, 1-ephenamine, methylpiperidine, arginine, lysine, ethylene-diamine or 2-phenylethylamine.

The compounds according to the invention can also be present in the form of their solvates, in particular in the form of their hydrates.

Moreover, the invention also includes prodrugs of the compounds according to the invention. According to the invention, "prodrugs" are derivatives of the compounds of the general formula (I) which for their part can be biologically less active or even inactive, but, following administration, are converted under physiological conditions into the corresponding biologically active form (for example metabolically, solvolytically or by another route).

Preference is given to compounds of the general formula (I) in which

X represents O, S, $CH_2$ or $CF_2$, $R^1$ and $R^2$ are identical or different and represent hydrogen or methyl, $R^3$ and $R^4$ are identical or different and represent hydrogen, halogen, $(C_1-C_4)$-alkyl, $CF_3$, $CHF_2$, $CH_2F$, vinyl or $(C_3-C_5)$-cycloalkyl, where at least one of the two substituents is not hydrogen, $R^5$ represents hydrogen, $(C_1-C_3)$-alkyl, fluorine, chlorine or bromine, $R^6$ represents a group of the formula $—S(O)_2—R^{10}$, $—NR^{11}—C(O)—R^{12}$, $—CH_2—R^{13}$ or $—M—R^{14}$, in which $R^{10}$ represents $NR^{16}R^{17}$, $(C_1-C_8)$-alkyl, $(C_5-C_7)$-cycloalkyl, phenyl, benzyl or represents a saturated, partially unsaturated or aromatic 5- to 10-membered heterocycle having up to three identical or different heteroatoms from the group consisting of N, O and S, where the abovementioned radicals are optionally substituted by one, two or three identical or different substituents selected from the group consisting of halogen, hydroxyl, oxo, cyano, nitro, amino, dimethyl-amino, trifluoromethyl, $(C_1-C_4)$-alkyl, $(C_1-C_4)$-alkoxy, $(C_3-C_6)$-cycloalkyl, phenyl, which for its parts is optionally substituted by halogen, $(C_1-C_4)$-alkyl, $(C_1-C_4)$-alkoxy, trifluoromethyl, nitro or cyano, $—C(O)—OR^{22}$, $—C(O)—NR^{23}R^{24}$, $—SO_2—NR^{25}R^{26}$, $—NH—C(O)—R^{27}$ and $—NH—C(O)—OR^{28}$, where $R^{22}$, $R^{23}$, $R^{24}$, $R^{25}$, $R^{26}$, $R^{27}$ and $R^{28}$ are identical or different and each represents hydrogen, phenyl, benzyl, $(C_1-C_4)$-alkyl or $(C_5-C_7)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino or $(C_1-C_5)$-alkanoyloxy, and $R^{16}$ and $R^{17}$ are identical or different and independently of one another represent hydrogen, straight-chain or branched $(C_1-C_6)$-alkyl which may be mono- or polysubstituted by identical or different substituents from the group consisting of $(C_1-C_4)$-alkoxy, $(C_1-C_4)$-alkoxycarbonyl, carboxyl, pyridyl or phenyl, where the latter for its part is optionally substituted by halogen, trifluoromethyl, $(C_1-C_4)$-alkyl or $(C_1-C_4)$-alkoxy, represent $(C_5-C_7)$-cycloalkyl or represent a 5- to 7-membered heterocycle which contains one or two nitrogen atoms, where cycloalkyl and heterocycle are optionally substituted by $(C_1-C_4)$-alkyl, or $R^{16}$ and $R^{17}$ together with the nitrogen atom to which they are attached form a 5- to 7-membered saturated heterocycle which may contain up to two further heteroatoms from the group consisting of N, O and S and which may be substituted by amino, $(C_1-C_4)$-alkyl, $(C_1-C_4)$-alkoxycarbonyl, $(C_1-C_4)$-alkoxycarbonylamino or phenyl, $R^{11}$ represents hydrogen, straight-chain or branched $(C_1-C_4)$-alkyl, benzyl, $(C_3-C_7)$-cycloalkyl or represents a 5- to 7-membered heterocycle which contains one or two nitrogen atoms, where cycloalkyl and heterocycle are optionally substituted by $(C_1-C_4)$-alkyl, $R^{12}$ represents straight-chain or branched $(C_1-C_8)$-alkyl which may be substituted by $(C_3-C_7)$-cycloalkyl, $(C_1-C_4)$-alkoxy, phenyl, phenoxy or benzyloxy, where the aromatic radicals mentioned for their part may each be substituted up to three times by identical or different substituents from the group consisting of halogen, $(C_1-C_4)$-alkyl and $(C_1-C_4)$-alkoxy, or represents phenyl which may be substituted up to three times by identical or different substituents from the group consisting of $(C_1-C_4)$-alkyl, $(C_1-C_4)$-alkoxy, halogen, cyano, amino and trifluoromethyl, or
represents a group of the formula $-OR^{29}$ or $-NR^{30}R^{31}$, in which
$R^{29}$ represents straight-chain or branched $(C_1-C_4)$-alkyl, and
$R^{30}$ and $R^{31}$ are identical or different and independently of one another
represent hydrogen, straight-chain or branched $(C_1-C_8)$-alkyl which may be substituted by phenyl, which for its part is optionally substituted up to two times by identical or different substituents from the group consisting of halogen, $(C_1-C_4)$-alkyl, trifluoromethyl and $(C_1-C_4)$-alkoxy,
represent $(C_3-C_7)$-cycloalkyl which may be substituted by $(C_1-C_4)$-alkyl, or
represent phenyl which may be substituted up to three times by identical or different substituents from the group consisting of halogen, $(C_1-C_4)$-alkyl, trifluoromethyl, $(C_1-C_4)$-alkoxy and amino, or
$R^{30}$ and $R^{31}$ together with the nitrogen atom to which they are attached form a 5- to 7-membered saturated heterocycle which may contain up to two further heteroatoms from the group consisting of N, O and S and which may be substituted by amino, $(C_1-C_4)$-alkyl, $(C_1-C_4)$-alkanoyl, aminocarbonyl, $(C_1-C_4)$-alkoxycarbonyl, $(C_1-C_4)$-alkoxycarbonylamino or phenyl,
$R^{13}$ represents a saturated, partially unsaturated or aromatic 5- or 6-membered heterocycle having up to three identical or different heteroatoms from the group consisting of N, O and S, which is optionally substituted by one, two or three identical or different substituents selected from the group consisting of $(C_1-C_4)$-alkyl, hydroxyl, oxo, $(C_1-C_4)$-alkoxy, halogen, cyano, carboxyl and $(C_1-C_4)$-alkoxycarbonyl, or
represents the group $-NR^{34}R^{35}$, in which
$R^{34}$ and $R^{35}$ are identical or different and represent hydrogen, $(C_1-C_6)$-alkyl, which may be substituted by phenyl, represent $(C_5-C_7)$-cycloalkyl, phenyl or represent 5- or 6-membered heteroaryl having up to three identical or different heteroatoms from the group consisting of N, O and S, where phenyl and heteroaryl for their part are each optionally mono- or disubstituted by identical or different substituents from the group consisting of hydroxyl, amino, cyano, halogen, $(C_1-C_4)$-alkyl, trifluoromethyl, $(C_1-C_4)$-alkoxy, carboxyl or $(C_1-C_4)$-alkoxycarbonyl,
M represents C=O, CH(OH) or $CF_2$, and
$R^{14}$ has the meaning of $R^{10}$ given above,
$R^7$ represents hydrogen, methyl or acetyl, and
Z represents a group of the formula

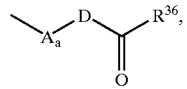

in which
A represents O or S,
a represents the number 0 or 1,
D represents a straight-chain $(C_1-C_3)$-alkylene group which may be mono- or polysubstituted by identical or different substituents from the group consisting of methyl, hydroxyl and fluorine, and
$R^{36}$ represents $OR^{37}$ or $NR^{38}R^{39}$, in which
$R^{37}$ represents hydrogen, phenyl, benzyl, $(C_1-C_6)$-alkyl or $(C_3-C_7)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy and a heterocycle, and
$R^{38}$ and $R^{39}$ are identical or different and each represents hydrogen, $(C_1-C_6)$-alkyl or $(C_3-C_7)$-cycloalkyl, which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle and phenyl which for its part is optionally substituted by halogen or hydroxyl,
and their pharmaceutically acceptable salts, solvates, hydrates and hydrates of the salts.

Particular preference is given to compounds of the general formula (I) in which
X represents O, S or $CH_2$,
$R^1$ and $R^2$ represent hydrogen,
$R^3$ and $R^4$ are identical or different and represent methyl, ethyl, propyl, isopropyl, cyclopropyl, trifluoromethyl, chlorine or bromine,
$R^5$ represents hydrogen,
$R^6$ represents a group of the formula $-S(O)_2-R^{10}$, $-NH-C(O)-R^{12}$, $-CH_2-R^{13}$, $-C(O)-R^{14}$ or $-CH(OH)-R^{40}$, in which
$R^{10}$ represents phenyl or represents 5- or 6-membered heteroaryl having up to three identical or different heteroatoms from the group consisting of N, O and S, which radicals are optionally mono- or disubstituted by identical or different substituents from the group consisting of fluorine, chlorine, bromine, hydroxyl, cyano, trifluoromethyl, $(C_1-C_4)$-alkyl, $(C_1-C_4)$-alkoxy, carboxyl and $(C_1-C_4)$-alkoxycarbonyl, or
represents the group $-NR^{16}R^{17}$, in which
$R^{16}$ and $R^{17}$ together with the nitrogen atom to which they are attached form a 5- or 6-membered saturated heterocycle which may contain a further heteroatom from the group consisting of N, O and S and which may be substituted by $(C_1-C_4)$-alkyl,
$R^{12}$ represents straight-chain or branched $(C_1-C_6)$-alkyl which is optionally substituted by phenoxy or benzyloxy,
$R^{13}$ represents 5- or 6-membered heteroaryl having up to three identical or different heteroatoms from the group consisting of N, O and S, which is optionally substituted by one or two identical or different substituents selected from the group consisting of $(C_1-C_4)$-alkyl, hydroxyl, $(C_1-C_4)$-alkoxy, fluorine, chlorine, bromine, cyano, carboxyl and $(C_1-C_4)$-alkoxycarbonyl, or represents the group $-NR^{34}R^{35}$, in which
$R^{34}$ represents $(C_1-C_6)$-alkyl or $(C_5-C_7)$-cycloalkyl, and $R^{35}$ represents benzyl which is optionally substituted in the phenyl ring by hydroxyl, $(C_1-C_4)$-alkoxy, $(C_1-C_4)$-alkyl, trifluoro-methyl, fluorine, chlorine or cyano, $R^{14}$ represents a group of the formula $—NR^{41}R^{42}$, in which $R^{41}$ represents hydrogen, $(C_1-C_6)$-alkyl or $(C_5-C_7)$-cycloalkyl, $R^{42}$ represents hydrogen or represents $(C_1-C_4)$-alkyl which may be substituted by phenyl, or $R^{41}$ and $R^{42}$ together with the nitrogen atom to which they are attached form a 5- or 6-membered saturated heterocycle which may contain a further heteroatom from the group consisting of N, O and S and which may be substituted by $(C_1-C_4)$-alkyl, and $R^{40}$ represents phenyl or naphthyl, which are optionally mono- or disubstituted by identical or different substituents from the group consisting of fluorine, chlorine, bromine, $(C_1-C_4)$-alkyl, $(C_1-C_4)$-alkoxy, cyano, trifluoromethyl or $(C_1-C_4)$-alkoxycarbonyl, $R^7$ represents hydrogen, and Z represents a group of the formula

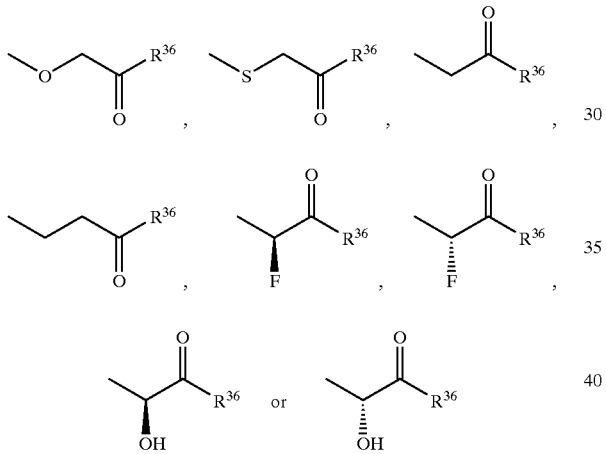

in which $R^{36}$ represents hydroxyl or the radical $—C(O)—R^{36}$ has the meanings of $R^{36}$ given above for a group which, in the sense of a prodrug, can be degraded to the carboxylic acid $—C(O)—OH$ or a salt thereof, and their pharmaceutically acceptable salts, solvates, hydrates and hydrates of the Particular preference is also given to compounds of the general formula (I) in which Z represents a group of the formula

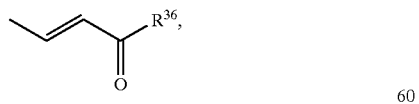

in which $R^{36}$ represents hydroxyl or the radical $—C(O)—R^{36}$ has the meanings of $R^{36}$ given above or a group which, in the sense of a prodrug, can be degraded to the carboxylic acid $—C(O)—OH$ or a salt thereof, and X, $R^1$, $R^2$, $R^3$, $R^4$, $R^5$, $R^6$ and $R^7$ are as defined above.

Very particular preference is given to compounds of the general formula (I) in which X represents $CH_2$ or, in particular, oxygen, $R^1$ and $R^2$ represent hydrogen, $R^3$ and $R^4$ are identical or different and represent methyl, ethyl, propyl, isopropyl, cyclopropyl, trifluoromethyl, chlorine or bromine, $R^5$ represents hydrogen, $R^6$ represents a group of the formula $—S(O)_2—R^{10}$, $—CH_2—R^{13}$ or $—C(O)—R^{14}$, in which $R^{10}$ represents phenyl, pyridyl, pyrimidinyl or pyridazinyl which are optionally mono- or disubstituted by identical or different substituents from the group consisting of fluorine, chlorine, bromine, hydroxyl, cyano, trifluoromethyl, $(C_1-C_4)$-alkyl, $(C_1-C_4)$-alkoxy, carboxyl and $(C_1-C_4)$-alkoxycarbonyl, or represents a group of the formula

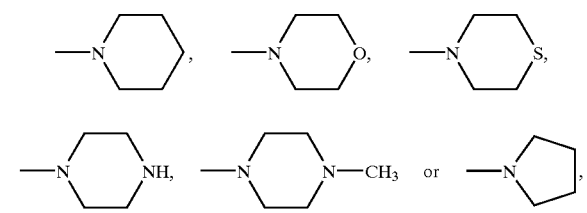

$R^{13}$ represents pyridyl, pyrimidinyl or pyridazinyl which are optionally substituted by one or two identical or different substituents selected from the group consisting of $(C_1-C_4)$-alkyl, hydroxyl, $(C_1-C_4)$-alkoxy, fluorine, chlorine, bromine, cyano, carboxyl and $(C_1-C_4)$-alkoxycarbonyl, or represents the group $—NR^{34}R^{35}$, in which $R^{34}$ represents $(C_1-C_4)$-alkyl or $(C_5-C_7)$-cycloalkyl, and $R^{35}$ represents benzyl which is optionally substituted in the phenyl ring by hydroxyl, $(C_1-C_4)$-alkoxy, $(C_1-C_4)$-alkyl, trifluoromethyl, fluorine, chlorine or cyano, and $R^{14}$ represents a group of the formula $—NR^{41}R^{42}$, in which $R^{41}$ represents hydrogen, $(C_1-C_4)$-alkyl or $(C_5-C_7)$-cycloalkyl, and $R^{42}$ represents hydrogen or represents $(C_1-C_4)$-alkyl which may be substituted by phenyl, $R^7$ represents hydrogen, and Z represents a group of the formula

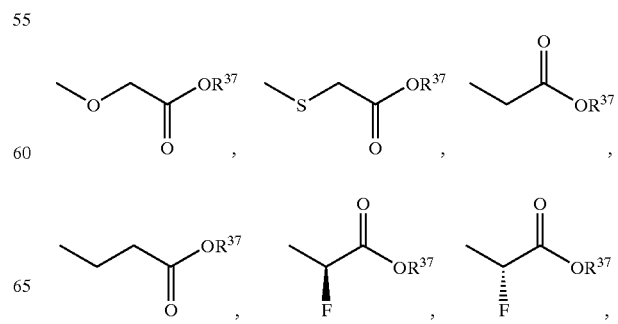

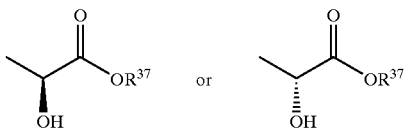

in which $R^{37}$ represents hydrogen, $(C_1-C_4)$-alkyl or $(C_4-C_6)$-cycloalkyl, and their pharmaceutically acceptable salts, solvates, hydrates and hydrates of the salts.

Very particular preference is also given to compounds of the general formula (I) in which Z represents a group of the formula

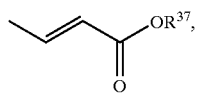

in which $R^{37}$ represents hydrogen, $(C_1-C_4)$-alkyl or $(C_4-C_6)$-cycloalkyl, and X, $R^1$, $R^2$, $R^3$, $R^4$, $R^5$, $R^6$ and $R^7$ are as defined above.

The general or preferred radical definitions given above apply both to the end products of the formula (I) and, correspondingly, to the starting materials or intermediates required in each case for the preparation.

Independently of the combinations of the radicals given in each case, the individual radical definitions given in the respective combinations or preferred combinations of radicals are also replaced by any radical definitions of other combinations.

Of particular importance are compounds of the formula (I) in which X represents methylene or oxygen.

Of particular importance are compounds of the formula (I) in which Z represents a group of the formula

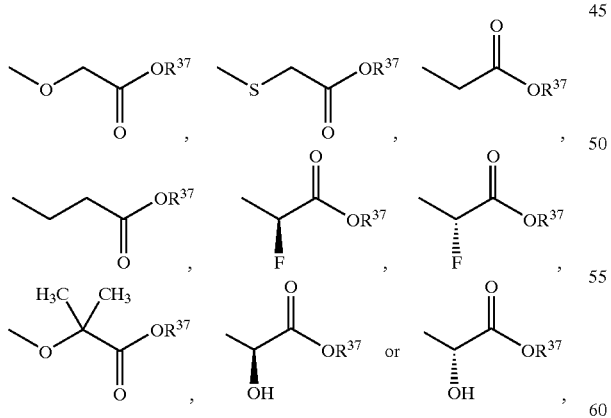

in which $R^{37}$ represents hydrogen, methyl or ethyl.

Of particular importance are compounds of the formula (I) in which Z represents a group of the formula

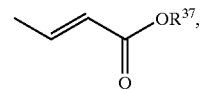

in which $R^{37}$ represents hydrogen, methyl or ethyl.

Of particular importance are compounds of the formula (I) in which $R^6$ represents a group of the formula $—S(O)_2—R^{10}$, in which $R^{10}$ represents phenyl or represents 5- or 6-membered heteroaryl having up to two identical or different heteroatoms from the group consisting of N, O and S, which radicals are optionally mono- or disubstituted by identical or different substituents from the group consisting of fluorine, chlorine, bromine, hydroxyl, cyano, trifluoromethyl, $(C_1-C_4)$-alkyl, $(C_1-C_4)$-alkoxy, carboxyl and $(C_1-C_4)$-alkoxycarbonyl, or represents the group $—NR^{16}R^{17}$, in which
$R^{16}$ and $R^{17}$ together with the nitrogen atom to which they are attached form a 5- or 6-membered saturated heterocycle which may contain a further heteroatom from the group consisting of N, O and S and which may be substituted by $(C_1-C4)$-alkyl.

Of particular importance are compounds of the formula (Ia)

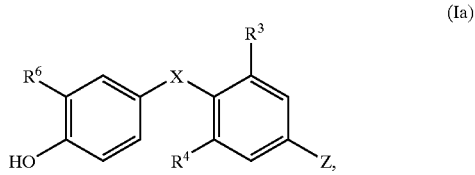

(Ia)

in which

X represents $CH_2$ or O, $R^3$ and $R^4$ are identical or different and represent bromine, trifluoromethyl, ethyl, cyclopropyl and, in particular, methyl or chlorine, Z represents a group of the formula $—CH_2—C(O)—OH$, $—CH_2—CH_2—C(O)—OH$, $—O—CH_2—C(O)—OH$, $—O—C[(CH_3)_2]—C(O)—OH$ or $—S—CH_2—C(O)—OH$, and $R^6$ represents a group of the formula $—S(O)_2—R^{10}$, in which
$R^{10}$ represents phenyl or represents pyridyl which are optionally mono- or disubstituted by identical or different substituents from the group consisting of fluorine, chlorine, cyano, trifluoromethyl, methyl, hydroxyl and methoxy.

Of very particular importance are also compounds of the formula (Ia) in which

Z represents a group of the formula $—CH=CH—C(O)—OH$ and

X, $R^3$, $R^4$ and $R^6$ are as defined above.

By way of example and by way of preference, the following individual compounds may be mentioned:

Compounds of the formula 1 in which Z has the meanings given in Table 1 (in the table, * denotes the point of attachment):

TABLE 1
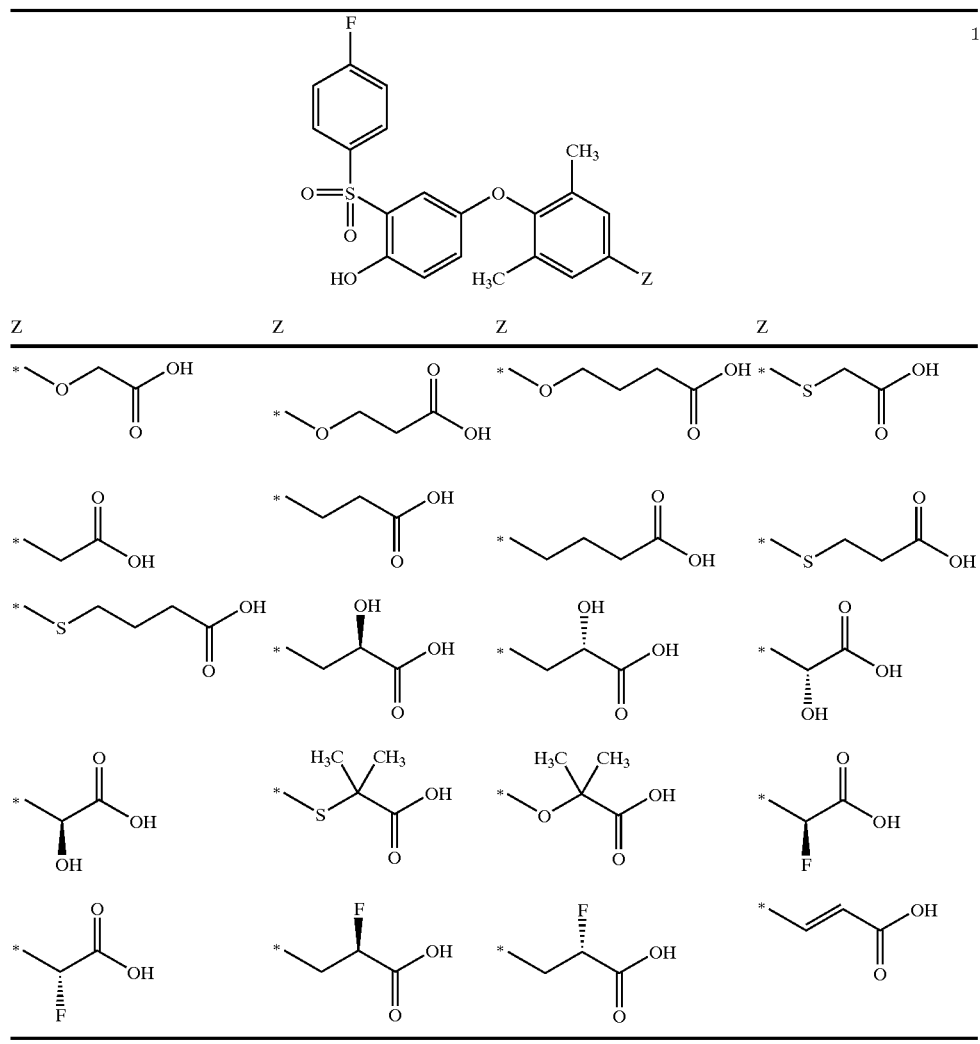
Individual compounds of the formula 2 in which Z in each case has the meanings given in Table 1 and for each of the individual compounds 1 to 20 $R^3$, instead of methyl in formula 1, has in each case the meanings given for $R^3$ in Table 2:
TABLE 2
TABLE 2-continued
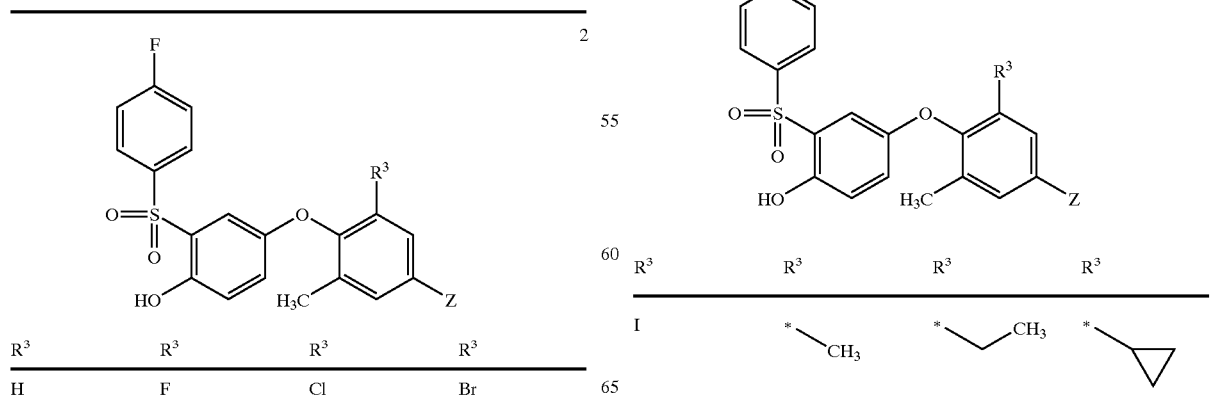

TABLE 2-continued (2)

[Structure: 4-fluorophenylsulfonyl group attached to a hydroxyphenyl ether linked to a methyl-substituted phenyl ring with R³ and Z substituents]

| R³ | R³ | R³ | R³ |
|---|---|---|---|
| *―CH=CH₂ | *―CH(CH₃)CH₃ | *―CF₃ | *―CF₂H |
| *―CFH₂ | | | |

Individual compounds of the formula 3 in which Z and R³ in each case have the meanings given in Tables 1 and 2 and for each of the individual compounds 1 to 260 R⁴, instead of methyl in formula 2, has in each case the meanings given for R⁴ in Table 3:

TABLE 3

(3)

[Structure: 4-fluorophenylsulfonyl group attached to a hydroxyphenyl ether linked to a phenyl ring with R³, R⁴ and Z substituents]

| R⁴ | R⁴ | R⁴ | R⁴ |
|---|---|---|---|
| H | F | Cl | Br |
| I | *―CH₃ | *―CH₂CH₃ | *―cyclopropyl |
| *―CH=CH₂ | *―CH(CH₃)CH₃ | *―CF₃ | *―CF₂H |
| *―CFH₂ | | | |

Individual compounds of the formula 4 in which Z, R³ and R⁴ in each case have the meanings given in Tables 1, 2 and 3 and for each of the individual compounds 1 to 3380 R⁶, instead of p-fluorophenylsulphonyl in formula 3, has in each case the meanings given for R⁶ in Table 4:

TABLE 4

(4)

[Structure: R⁶-substituted hydroxyphenyl ether linked to a phenyl ring with R³, R⁴ and Z substituents]

| R⁶ | R⁶ | R⁶ | R⁶ |
|---|---|---|---|
| *―SO₂―phenyl | *―SO₂―(4-F-phenyl) | *―SO₂―(4-Cl-phenyl) | *―SO₂―(4-CH₃-phenyl) |
| *―SO₂―(4-pyridyl) | *―SO₂―(4-OCH₃-phenyl) | *―SO₂―(4-CF₃-phenyl) | *―CH₂―(2-CH₃,3-CH₃-5-pyridyl) |
| *―CH₂―(4-pyridyl) | *―CH₂―(3-pyridyl) | *―CH₂―(2-pyridyl) | *―CH₂―(6-oxo-1H-pyridazin-3-yl) |

TABLE 4-continued

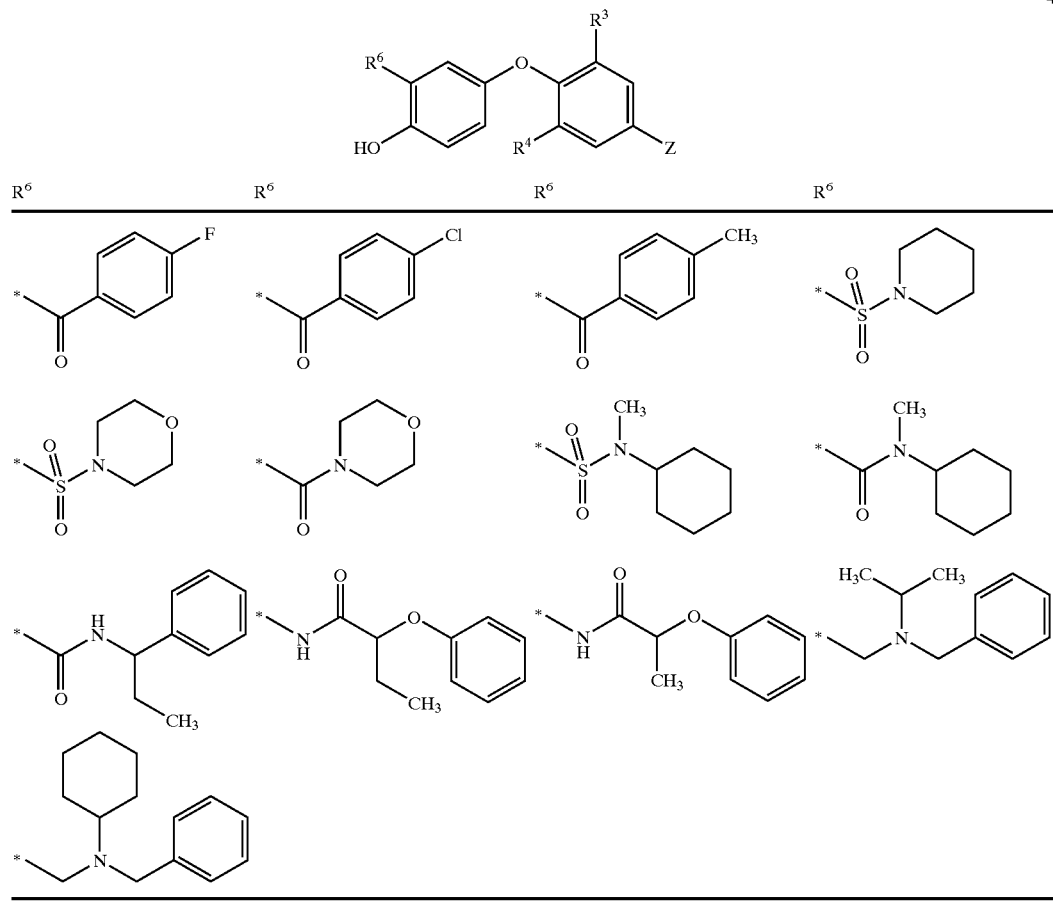

The compounds of the general formula (I) according to the invention can be prepared according to one of the process variants [A], [B] or [C] below by reacting reactive phenol derivatives of the general formulae (IIa–c) with reactive phenyl derivatives of the general formulae (IIIa–c), if appropriate in the presence of inert solvents and catalysts and if appropriate with isolation of the intermediates of the general formulae (IV), (IVa), (IVb) or (IVc) or directly, to give compounds of the formula (I) in which the substituents $R^1$, $R^2$, $R^3$, $R^4$, $R^5$ and $R^6$ and X and Z are in each case as defined above, Z' has the meaning given for Z or represents OH, O—PG, SH, S—PG, or represents a nitro, aldehyde, cyano, carboxyl or ($C_1$–$C_4$)-alkoxycarbonyl group, and PG represents a suitable protective group.

Process variant [A]:

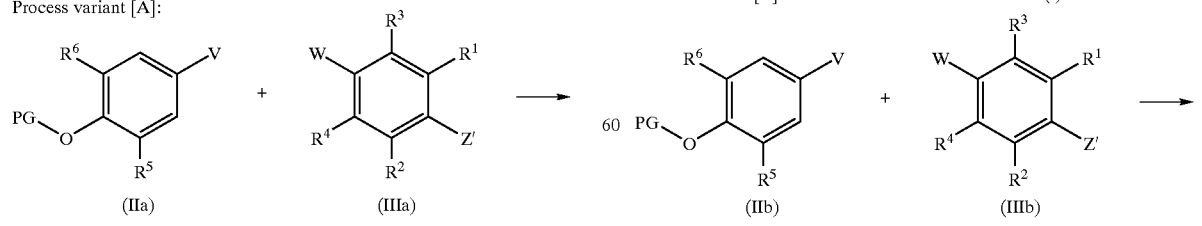

V = F, Cl, Br, I, B(OH)$_2$; W = OH, SH, NH$_2$
or V = OH, SH, NH$_2$; W = F, Cl, Br, I, B(OH)$_2$

Process variant [B]:

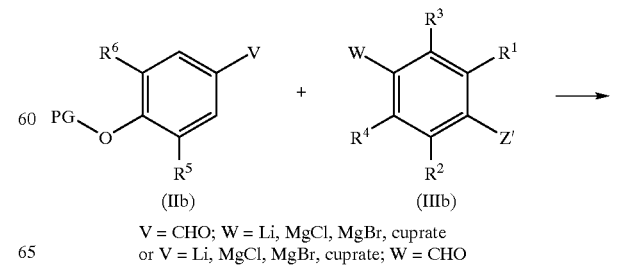

V = CHO; W = Li, MgCl, MgBr, cuprate
or V = Li, MgCl, MgBr, cuprate; W = CHO

-continued

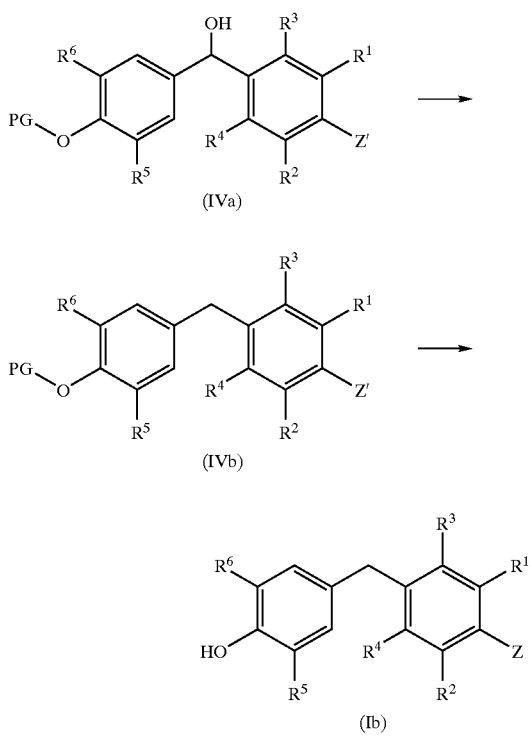

Process variant [C]:

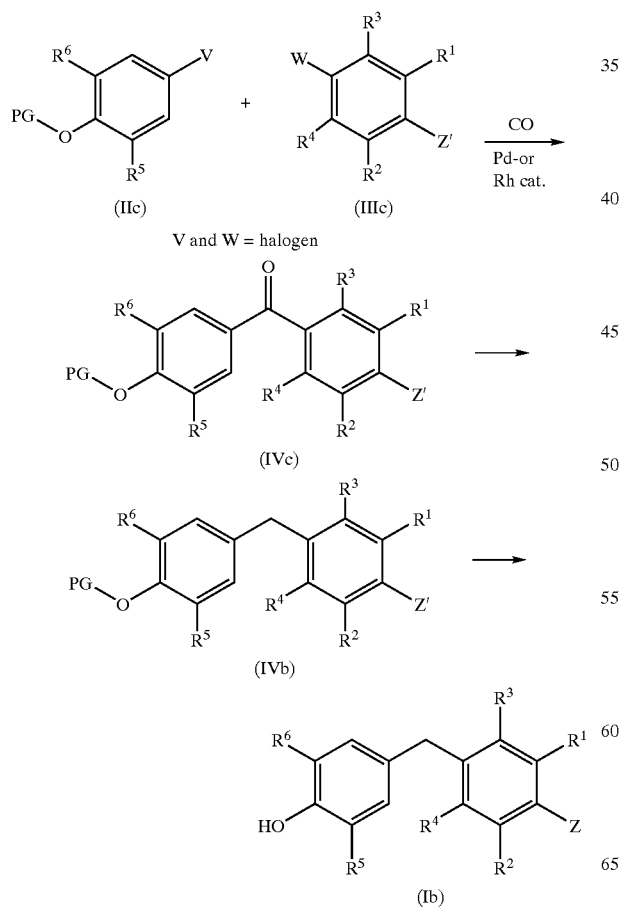

Catalysts which may be mentioned by way of example are coupling catalysts such as Pd, Rh and/or Cu compounds.

Examples of the reactive groups V and W that may be mentioned are: halogen, hydroxyl, $CH_2Br$, mercapto, amino, CHO, Li, magnesium, tin, boron or copper derivatives.

The phenol derivatives of the general formulae (IIa–c) which can be used according to the invention are known or can be prepared by known methods [compare, for example, Gurumani et al., Indian Journal of Chemistry 32B, 281–287 (1993); Riering et al., Chem. Ber. 127, 859–874 (1994)].

The phenyl derivatives of the general formulae (IIIa–c) are likewise known or can be prepared by known methods [compare, for example, van de Bunt, Recl. Trav. Chim. Pays-Bas 48, 131 (1929); Valkanas, J. Chem. Soc., 5554 (1963); Thea et al., J. Org. Chem. 50, 1867–1872 (1985); Baker et al., J. Chem. Soc., 2303–2306 (1948)].

The reaction of the starting materials (IIa–c) with (IIIa–c) is generally carried out at atmospheric pressure. However, it can also be carried out under elevated or reduced pressure.

The reaction can be carried out in a temperature range of from −100° C. to +200° C., preferably from −78° C. to +150° C., in the presence of inert solvents. Inert solvents which may be mentioned as being preferred are: dimethylsulphoxide (DMSO), dimethylformamide (DMF), N-methyl-2-pyrrolidinone (NMP), tetrahydrofuran (THF), diethyl ether, dichloromethane, etc.

Depending on the specific pattern of substituents, it is also possible that, in the reaction of (IIa–c) with (IIIa–c), intermediates of the formula (IV), (IVa), (IVb) or (IVc) are formed in which, for example, the substituent Z' represents a nitro, aldehyde, cyano, carboxyl or alkoxycarbonyl group or X represents a CH(OH)— or C(O) group, which intermediates can then, with or without isolation, convert it further by customary methods into compounds of the formula (I).

The processes according to the invention can be illustrated in an exemplary manner by the following formula schemes:

Scheme 1:

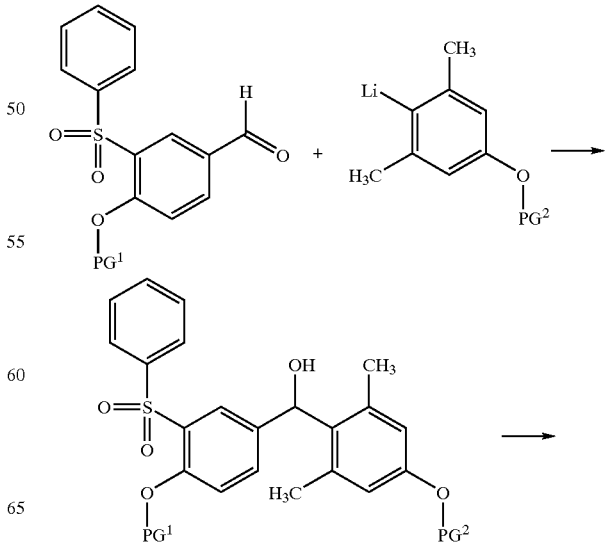

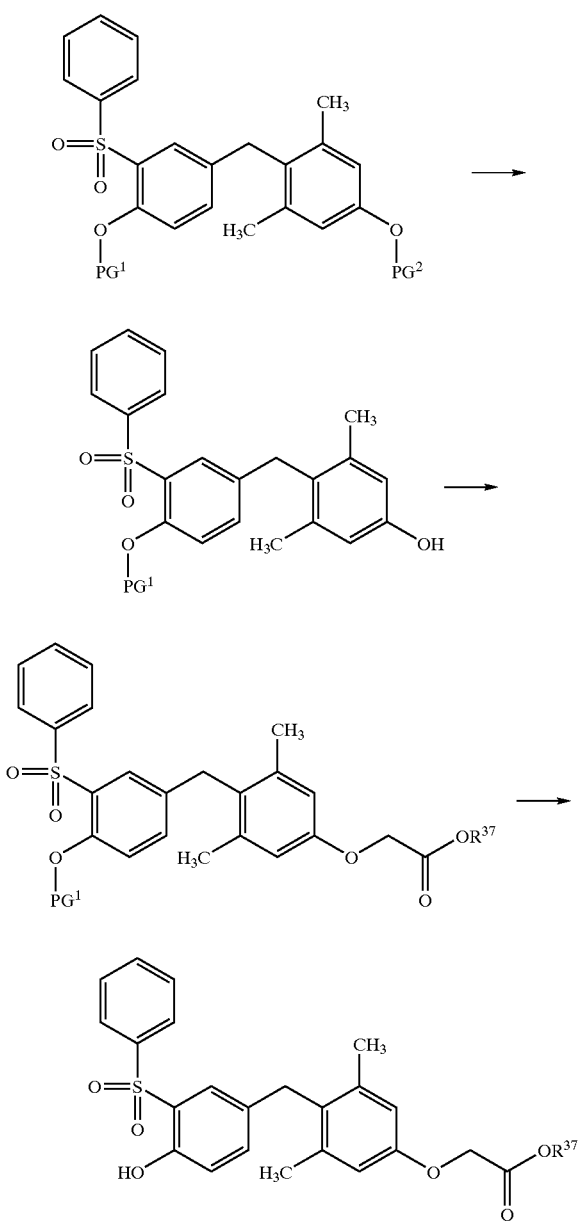
Scheme 2:
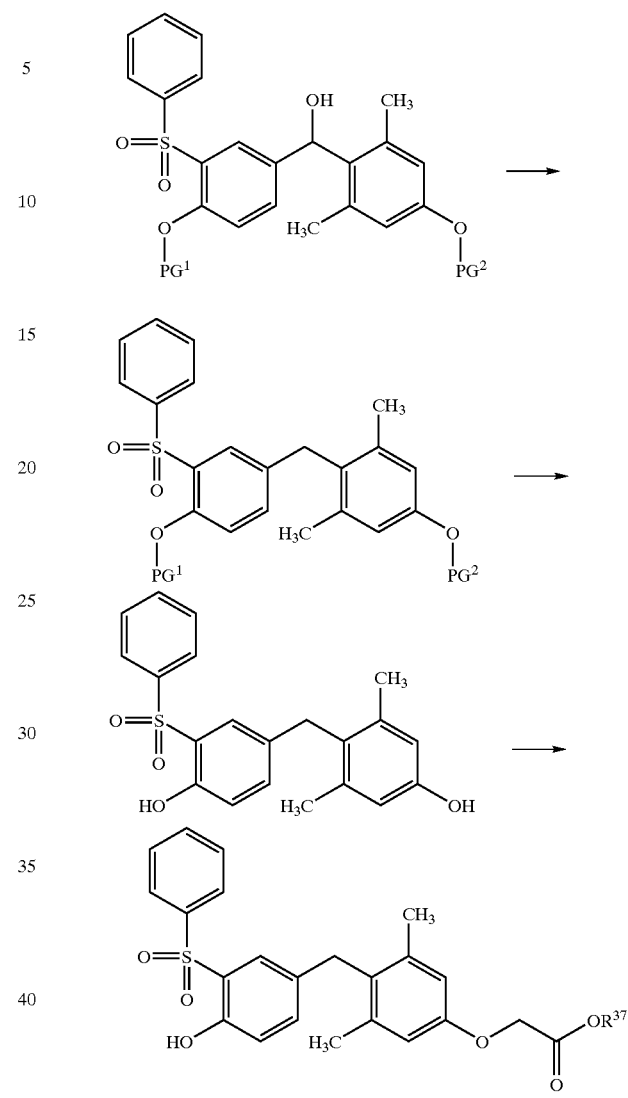
Scheme 3:
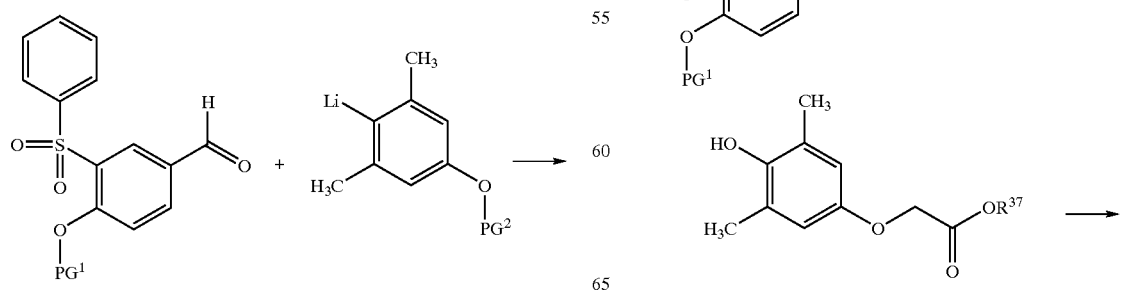

-continued

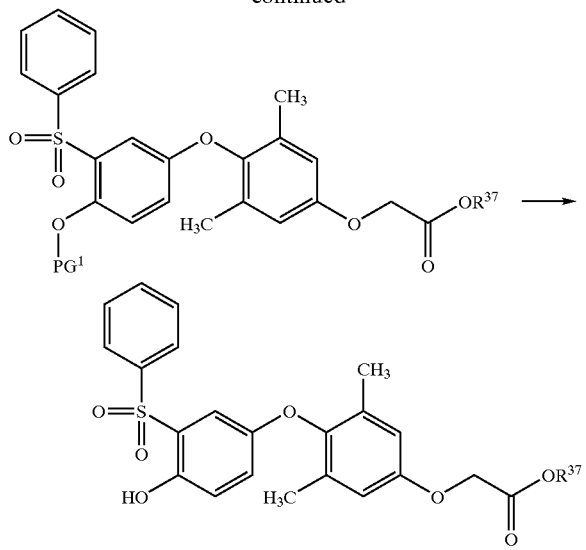

Depending on the meaning of the substituents $R^1$, $R^2$, $R^3$, $R^4$, $R^5$ and $R^6$, it may be advantageous or necessary to vary the scope of meanings given in individual process steps.

In the present application, protective groups (PG, $PG^1$, $PG^2$) are understood as meaning groups in starting materials and/or intermediates which protect the functional groups present, such as, for example, carboxyl, amino, mercapto or hydroxyl groups, and which are customary in preparative organic chemistry. The groups protected in this manner can then be converted in a simple manner under known conditions in free functional groups.

The compounds of the formula (I) according to the invention have a surprising and useful spectrum of pharmacological activity and can therefore be used as versatile medicaments for treating humans and mammals, such as, in particular, dogs and cats. In particular, they can be used for all indications which can be treated with natural thyroid hormones, such as, by way of example and by way of preference, depression, goitre or cancer of the thyroid gland. The compounds of the formula (I) according to the invention are preferably used to treat arteriosclerosis, hypercholesterolaemia, dyslipidaemia and obesity. Furthermore, it is also possible to use the compounds according to the invention to treat cardiac insufficiency and to achieve postprandial lowering of triglycerides.

The compounds are also suitable for treating certain respiratory disorders, i.e., in particular, pulmonary emphysema, and for medicinally promoting maturation of the lungs.

The compounds are furthermore suitable for treating pain and migraine, for neuronal repair (remyelinization) and for treating Alzheimer's disease.

The compounds are furthermore suitable for treating osteoporosis, cardiac arrhythmias, hypothyroidism and skin disorders.

Moreover, the compounds can also be used for promoting and regenerating hair growth, and for treating diabetes.

The active compounds according to the invention allow further treatment alternatives and are a useful addition to the pharmaceutical prior art. Compared with the known thyroid hormone preparations which have hitherto been used, the compounds according to the invention have an improved activity spectrum. They are preferably distinguished by high specificity, good compatibility and fewer adverse effects, in particular in the cardiovascular field.

The activity of the compounds according to the invention can be examined, for example, in vitro by the known T3 promoter assay cell test, described below:

The test is carried out using a stably transfected human HepG2 hepatocarcinoma cell which expresses a luciferase gene under the control of a thyroid-hormone-regulated promoter. The vector used for transfection carries, upstream of the luciferase gene, a minimal thymidine kinase promoter with a thyroid-hormone-responsive element (TRE) comprising two inverted palindromes of in each case 12 bp and one 8 bp spacer.

For the test, the cell cultures are sown in 96-well plates in Eagle's Minimal Essential Medium, with the following additives: glutamine, tricine, [N-(tris-hydroxymethyl)-methyl)glycine], sodium pyruvate, non-essential amino acids (L-Ala, L-Asn, L-Asp, L-Pro, L-Ser, L-Glu, Gly), insulin, selenium and transferrin. The cultures are grown at 37° C. in a 10% $CO_2$ atmosphere for 48 hours. Serial dilutions of test substance or reference compound (T3, T4) and the costimulator retinoic acid are then added to the test cultures, which are then incubated as above for a further 48 or 72 hours. Each substance concentration is tested in four replications. To determine the luciferase, induced by T3 or other substances, the cells are then lyzed by addition of a triton- and luciferin-containing buffer (from Promega) and immediately measured luminometrically. For each compound, the $EC_{50}$ is calculated. In this test, the compound of Example 2 has an $EC_{50}$ of 2 nM.

In the test described below, too, the compounds according to the invention have surprisingly advantageous properties:
Description of the Test for Finding Pharmacologically Active Substances The substances to be examined in vivo for their serum-cholesterol-lowering action are administered orally to male mice having a body weight between 25 and 35 g. One day prior to the start of the test, the animals are divided into groups with the same number of animals, generally n=7–10. During the entire experiment, the animals have drinking water and feed ad libitum. The substances are administered orally once a day for 7 days. To this end, the test substances are dissolved in a solution of Solutol HS 15+ethanol+saline solution (0.9%) in a ratio of 1+1+8 or in a solution of Solutol HS 15+saline solution (0.9%) in a ratio of 2+8. The dissolved substances are administered in a volume of 10 ml/kg of body weight using a stomach tube. Animals which are treated exactly in the same manner but are only given the solvent (10 ml/kg of body weight), without test substance, serve as the control group.

Prior to the first substance administration, a blood sample is taken from each mouse by puncture of the retroorbital venus plexus to determine the serum cholesterol (prevalue). The test substance is then administered to the animals for the first time, using a stomach tube. 24 hours after the last substance administration (on the 8th day after the beginning of the treatment), once more a blood sample is taken from each animal by puncture of the retroorbital venus plexus to determine the serum cholesterol. The blood samples are centrifuged and, when the serum is obtained, the cholesterol is determined photometrically using an EPOS analyzer 5050 (Eppendorf-Gerätebau, Netheler & Hinz GmbH, Hamburg). The determination is carried out using a commercial enzyme test (Boehringer Mannheim, Mannheim).

The effect of the test substances on the serum cholesterol concentration is determined by subtracting the cholesterol value of the 1st blood sample (prevalue) from the cholesterol value of the 2nd blood sample (after the treatment). The mean of the differences of all cholesterol values of one group is determined and compared to the mean of the differences of the control group.

Statistical evaluation is carried out using Student's t-test, after the variants have been checked for homogeneity.

Substances which lower the serum cholesterol of the treated animals in a statistically significant manner (p<0.05) by at least 10%, compared to the value of the control group, are considered to be pharmacologically effective.

At the end of the experiments, the animals are weighed and, after blood samples have been taken, sacrificed. To check for potential cardiovascular side-effects under the influence of the substances, the hearts are removed and weighed. An effect on the cardiovascular system can be determined from a significant increase of the weight of the heart. A further parameter which can be used for assessing the effect of the substances is a change in body weight.

In an analogous manner, is it possible to use, for example, NMRI mice, ob-ob mice, Wistar rats or fa,fa sugar rats as test animals for this test.

A further in vivo test in which the compounds according to the invention show surprisingly advantageous properties is the animal model of the cholesterol-fed rat [A. Taylor et al., Molecular Pharmacology 52, 542–547 (1997); Z. Stephan et al., Atherosclerosis 126, 53–63 (1996)].

Furthermore, it is also possible to examine the cholesterol-lowering effect of the compounds according to the invention on normal cholesterolaemic dogs by oral administration of the test substances for 5–7 days.

A parameter which can be used to test the effectiveness of the compounds according to the invention in the treatment of obesity is, for example, the development of the body weight after an administration of this test substance for four weeks in mice in which obesity had been induced beforehand by feeding with high-fat feed.

To further examine potential cardiovascular side-effects under the influence of the substances, it is possible to use, inter alia, the determination of the expression of the mRNA of the "HCN2" ion channel ("hyperpolarization-activated cyclic nucleotide-gated channel") in the hearts of mice or rats [cf. also: Trost et al., Endocrinology 141 (9), 3057–3064 (2000); Gloss et al., Endocrinology 142 (2), 544–550 (2001); Pachuki et al., Circulation Research 85, 498–503 (1999)]:

HCN2 Assay

Quantification of the mRNA of the hyperpolarization-activated cyclic nucleotide-gated cation channel (HCN2) in the hearts of rats was carried out by real-time PCR (TaqMan-PCR; Heid et al., Genome Res. 6 (10), 986–994). To this end, after the preparation of the hearts, the total RNA was isolated using Rnaesy columns (from Qiagen), digested with DNase and then transcribed into cDNA (SUPERSCRIPT-II RT cDNA synthesis kit, from Gibco). The HCN2-mRNA was determined on an ABI Prism 7700 apparatus (from Applied Biosystems). The sequence of the forward and reverse primers was: 5'-GGGAATCGACTCCGAGGTC-3' and 5'-GATCTTGGTGAAACGCACGA-3', respectively, that of the fluorescent probe was 5'-6FAM-ACAAGACGGCCCGTGCACTACGC-TAMRA-3 (FAM= fluorescent dye 6-carboxyfluorescin; TAMRA=quencher 6-carboxytetramethylrhodamine). During the polymerase chain reaction, the 5'-exonuclease activity of the taq polymerase cleaves off the fluorescent dye FAM, giving the fluorescent signal which had been quenched beforehand. The threshold cycle (Ct value) recorded was the number of cycles at which the intensity of the fluorescence was 10 standard deviations above the background fluorescence. The relative expression of the HCN2-mRNA calculated in this manner was subsequently normalized for the expression of the ribosomal protein L32.

In an analogous manner, it is also possible to carry out this assay using the hearts of mice. In this case, the sequence of the forward and reverse primers was 5'-CGAGGTGCTGGAGGAATACC-3' and 5'-CTAGCCGGTCAATAGCCACAG-3', respectively, that of the fluorescent probe was 5'-6FAM-CATGATGCGGCGTGCCTTTGAG-TAMRA-3.

All customary administration forms, i.e. oral, parenteral, inhalative, nasal, sublingual, buccal, rectal or external, for example transdermal, particularly preferably oral or parenteral, are suitable for administering the compounds of the general formula (I). In the case of parenteral administration, intravenous, intramuscular and subcutaneous administration, for example as subcutaneous depot, may be mentioned as being particularly preferred. Very particular preference is given to oral administration.

To this end, the active compounds can be administered on their own or in the form of preparations. Suitable preparations for oral administration are, inter alia, tablets, capsules, pellets, sugar-coated tablets, pills, granules, solid and liquid aerosols, syrups, emulsions, suspensions and solutions. The active compound has to be present in such an amount that a therapeutic effect is obtained. In general, the active compound can be present in a concentration of from 0.1 to 100% by weight, in particular from 0.5 to 90% by weight, preferably from 5 to 80% by weight. In particular, the concentration of active compound should be 0.5–90% by weight, i.e. the active compound should be present in amounts which are sufficient to achieve the dosage range indicated.

To this end, the active compounds can be converted in a manner known per se into the customary preparations. This is carried out using inert nontoxic pharmaceutically suitable excipients, auxiliaries, solvents, vehicles, emulsifiers and/or dispersants.

Auxiliaries which may be mentioned are, for example: water, nontoxic organic solvents, such as, for example, paraffins, vegetable oils (for example sesame oil), alcohols (for example ethanol, glycerol), glycols (for example polyethylene glycol), solid excipients, such as natural or synthetic ground minerals (for example talc or silicates), sugars (for example lactose), emulsifiers, dispersants (for example polyvinylpyrrolidone) and lubricants (for example magnesium sulphate).

In the case of oral administration, tablets may, of course, also contain additives such as sodium citrate, together with fillers such as starch, gelatin and the like. Aqueous preparations for oral administration may furthermore be mixed with flavour enhancers or colorants.

In the case of oral administration, preference is given to administering dosages of from 0.001 to 5 mg/kg, preferably from 0.001 to 3 mg/kg, of body weight per 24 hours.

The novel active compounds can be administered on their own and, if required, also in combination with other active compounds, preferably from the group of the CETP inhibitors, antidiabetics, antioxidants, cytostatics, calcium antagonists, hypotensive agents, thyroid hormones, inhibitors of HMG-CoA reductase, inhibitors of HMG-CoA reductase gene expression, squalene synthase inhibitors, ACAT inhibitors, circulation-promoting agents, thrombocyte aggregation inhibitors, anticoagulants, angiotensin-II receptor antagonists, cholesterol absorption inhibitors, MTP inhibitors, aldose reductase inhibitors fibrates, niacin, anorectics, lipase inhibitors and PPAR agonists.

The embodiments below are meant to illustrate the invention in an exemplary manner, without limiting the scope of the invention.

| Abbreviations: | |
|---|---|
| DCI | direct chemical ionization (for MS) |
| DMF | N,N-Dimethylformamide |
| DMSO | Dimethyl sulphoxide |
| ESI | Electron spray ionization (for MS) |
| HPLC | High-pressure, high-performance liquid chromatography |
| lit. | Literature |
| MS | Mass spectroscopy |
| NMR | Nuclear magnetic resonance spectroscopy |
| $R_f$ | Retention index (for thin-layer chromatography) |
| RT | Room temperature |
| $R_t$ | Retention time (for HPLC) |
| THF | Tetrahydrofuran |

Starting Materials

EXAMPLE I

[4-(Benzyloxy)-3-bromophenyl]methanol

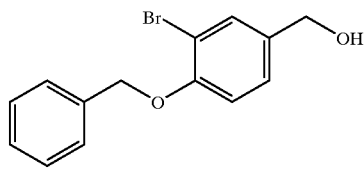

1.0 g (3.43 mmol) of 4-(benzyloxy)-3-bromobenzaldehyde [Lit.: R. Baker et al., J. Chem. Soc. Chem. Commun. 14, 1102–1104 (1987)] is initially charged in 10 ml of tetrahydrofuran. At 0° C., 0.04 g (1.03 mmol) of sodium borohydride is added. The reaction mixture is stirred at room temperature for 3 hours. Saturated ammonium chloride solution is then added, and the mixture is extracted twice with ethyl acetate. The combined organic phases are dried with sodium sulphate and the solvent is removed under reduced pressure. This gives 0.98 g (97% of theory) of [4-(benzyloxy)-3-bromophenyl]methanol.

$^1$H-NMR (200 MHz, CDCl$_3$): δ=1.62 (broad s, 1H), 4.6 (s, 2H), 5.16 (s, 2H), 6.86–6.93 (m, 1H), 7.11–7.59 (m, 7H).

EXAMPLE II

{[4-(Benzyloxy)-3-bromobenzyl]oxy}(tert-butyl)dimethylsilane

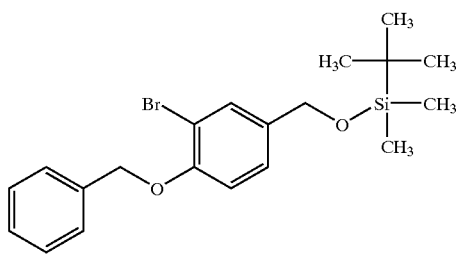

3.0 g (10.23 mmol) of [4-(benzyloxy)-3-bromophenyl]methanol (Example I) are initially charged in 30 ml of DMF. At room temperature, 1.39 g (12.28 mmol) of 1H-imidazole (60% pure) and 2.01 g (13.3 mmol) of tert-butyl(chloro)dimethylsilane are added. The reaction mixture is stirred at room temperature overnight. Water is then added, and the mixture is extracted three times with diethyl ether. The combined organic phases are washed three times with water and once with saturated sodium chloride solution. The organic phase is dried with sodium sulphate and the solvent is removed under reduced pressure. This gives 4.02 g (86% of theory) of {[4-(benzyloxy)-3-bromobenzyl]oxy}(tert-butyl)dimethylsilane.

$^1$H-NMR (200 MHz, CDCl$_3$): δ=0.015 (m, 6H), 0.80–0.88 (m, 9H), 4.55 (s, 2H), 5.06 (s, 2H), 6.80 (d, 1H), 7.08 (dd, 1H), 7.21–7.43 (m, 6H).

EXAMPLE III ({4-(Benzyloxy)-3-[(4-fluorophenyl)sulphanyl]benzyl}oxy)(tert-butyl)dimethylsilane

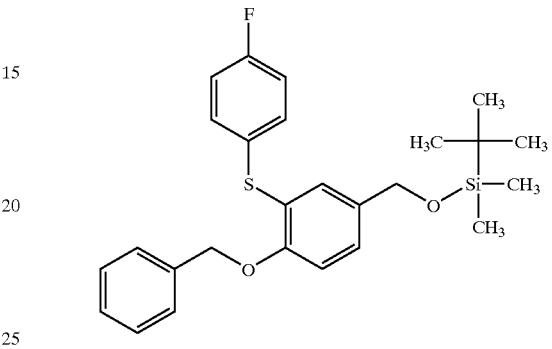

0.5 g (1.23 mmol) of {[4-(benzyloxy)-3-bromobenzyl]oxy}(tert-butyl)dimethylsilane (Example II) is dissolved in 12 ml of tetrahydrofuran. At −78° C., 0.55 ml (1.35 mmol) of tert-butyllithium (2.5 molar solution in hexane) is added dropwise, and the mixture is stirred for another 15 minutes. 0.34 g (1.35 mmol) of 4-fluorophenyl disulphide is then added. The mixture is then stirred at −78° C. for 1 hour. Saturated ammonium chloride solution is added, the mixture is extracted three times with ethyl acetate and the combined organic phases are dried with sodium sulphate. The product is purified by chromatography on silica gel 60 (mobile phase: cyclohexane). This gives 0.485 g (66% of theory) of ({4-(benzyloxy)-3-[(4-fluorophenyl)sulphanyl]benzyl}oxy)(tert-butyl)dimethylsilane.

$^1$H-NMR (200 MHz, CDCl$_3$): δ=0.00 (s, 6H), 0.85 (s, 9H), 4.55 (s, 2H), 5.11 (s, 2H), 6.83–7.04 (m, 6H), 7.24–7.38 (m, 6H).

EXAMPLE IV ({14-(Benzyloxy)-3-[(4-fluorophenyl)sulphonyl]benzyl}oxy)(tert-butyl)dimethylsilane

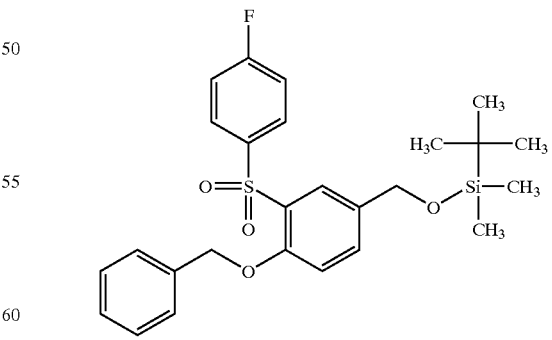

4.2 g (9.24 mmol) of ({4-(benzyloxy)-3-[(4-fluorophenyl)sulphanyl]benzyl}oxy)(ter-butyl)dimethylsilane (Example III) are dissolved in 25 ml of dichloromethane, and 7.33 g (21.25 mmol) of 3-chlorobenzeneperoxycarboxylic acid are added. The reaction mixture is stirred at room temperature overnight. The mixture is then washed twice with saturated sodium bicarbonate solution and then dried with sodium sulphate, and the solvent is removed under reduced pressure. The residue is purified by chromatography on silica gel 60 (mobile phase: cyclohexane/ethyl acetate 4:1). This gives 3.4 g (68% of theory) of ({4-(benzyloxy)-3-[(4-fluorophenyl)sulphonyl]benzyl}oxy)(tert-butyl)dimethylsilane.

$^1$H-NMR (200 MHz, CDCl$_3$): δ=0.00 (s, 6H), 0.81 (s, 9H), 4.61 (s, 2H), 4.90 (s, 2H), 6.75–6.84 (m, 3H), 7.07–7.18 (m, 2H), 7.23–7.28 (m, 3H), 7.40 (dd, 1H), 7.63–7.7 (m, 2H), 7.98 (d, 1H).

EXAMPLE V
{4-(Benzyloxy)-3-[(4-fluorophenyl)sulphonyl]phenyl}methanol

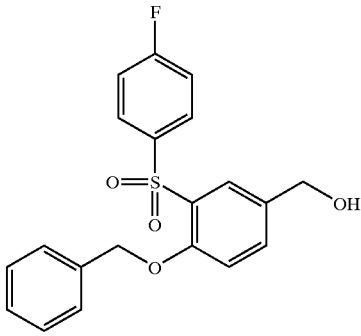

3.4 g (6.99 mmol) of ({4-(benzyloxy)-3-[(4-fluorophenyl)sulphonyl]benzyl}oxy)(tertbutyl)dimethylsilane (Example IV) are dissolved in 10 ml of tetrahydrofuran. At room temperature, 7.68 mmol of tetrabutylammonium fluoride trihydrate (1-molar solution in THF) are added. The mixture is stirred at room temperature overnight. The solvent is then removed under reduced pressure and the product is purified by chromatography on silica gel 60 (mobile phase: cyclohexane/ethyl acetate 3:2). This gives 2.1 g (81% of theory) of {4-(benzyloxy)-3-[(4-fluorophenyl)sulphonyl]phenyl}methanol.

$^1$H-NMR (200 MHz, CDCl$_3$): δ=1.77 (t, 1H), 4.72 (d, 2H), 5.05 (s, 2H), 6.86–6.96 (m, 3H), 7.22–7.40 (m, 2H), 7.35–7.40 (m, 3H), 7.55 (dd, 1H), 7.74–7.84 (m, 2H), 8.16 (d, 1H).

EXAMPLE VI
4-(Benzyloxy)-3-[(4-fluorophenyl)sulphonyl]benzaldehyde

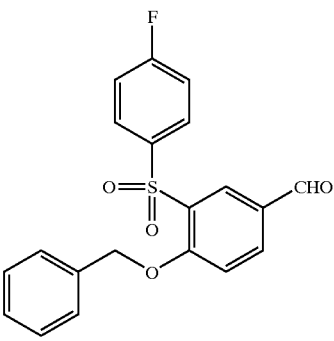

2.1 g (5.64 mmol) of {4-(benzyloxy)-3-[(4-fluorophenyl)sulphonyl]phenyl}methanol (Example V) are dissolved in 25 ml of dichloromethane. At room temperature, 4.9 g (56.39 mmol) of manganese(IV) oxide are added. The mixture is stirred at room temperature overnight. The reaction mixture is then filtered through Celite and the solvent is removed under reduced pressure. This gives 1.82 g (86% of theory) of 4-(benzyloxy)-3-[(4-fluorophenyl)sulphonyl]benzaldehyde.

$^1$H-NMR (200 MHz, CDCl$_3$): δ=5.12 (s, 2H), 6.87–6.99 (m, 2H), 7.1 (d, 1H), 7.24–7.30 (m, 2H), 7.41–7.46 (m, 3H), 7.72–7.82 (m, 2H), 8.08 (dd, 1H), 8.7 (d, 1H), 9.98 (s, 1H).

EXAMPLE VII
4-Bromo-3,5-dimethylphenyl triisopropylsilyl ether

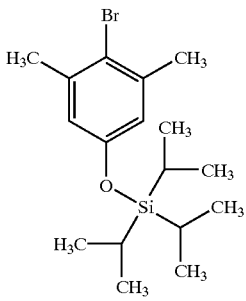

At room temperature, 5.0 g (24.87 mmol) of 4-bromo-3,5-dimethylphenol, 2.03 g (29.84 mmol) of imidazole and 6.23 g (32.33 mmol) of chloro(triisopropyl)silane are stirred in 20 ml of dimethylformamide overnight. Saturated sodium bicarbonate solution is then added, and the mixture is extracted three times with diethyl ether. The combined organic phases are washed with water and dried with sodium sulphate, and the solvent is removed under reduced pressure. This gives 7.5 g (84% of theory) of 4-bromo-3,5-dimethylphenyl triisopropylsilyl ether.

$^1$H-NMR (200 MHz, CDCl$_3$): δ=1.05–1.36 (m, 21H), 2.35 (s, 6H), 6.60 (s, 2H).

EXAMPLE VIII
{4-(Benzyloxy)-3-[(4-fluorophenyl)sulphonyl]phenyl}{2,6-dimethyl-4-[(triisopropylsilyl)oxy]phenyl}methanol

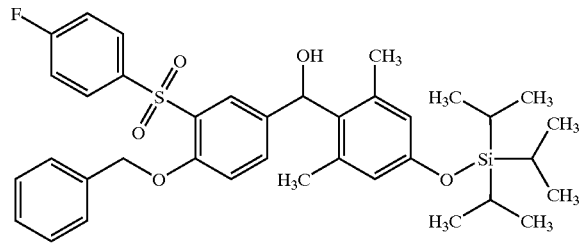

810 mg (2.27 mmol) of 4-bromo-3,5-dimethylphenyl triisopropylsilyl ether (Example VII) are dissolved in 10 ml of tetrahydrofuran. At −78° C., 147.3 mg (2.3 mmol) of butyllithium (2.4 molar in hexane) are added dropwise. At the same temperature, stirring is continued for one hour, and 600 mg (1.62 mmol) of 4-(benzyloxy)-3-[(4-fluorophenyl)sulphonyl]benzaldehyde (Example VI), dissolved in 4 ml of tetrahydrofuran, are then added dropwise. The mixture is stirred at −78° C. for one hour, and saturated ammonium chloride solution is then added. The mixture is extracted three times with ethyl acetate and the combined organic phases are dried with sodium sulphate and concentrated. This gives 580 mg (55% of theory) of {4-(benzyloxy)-3-[(4-fluorophenyl)sulphonyl]phenyl}{2,6-dimethyl-4-(triisopropylsilyl)oxy]phenyl}methanol.

¹H-NMR (200 MHz, CDCl₃): δ=1.04–1.35 (m, 21H), 2.2 (s, 6H), 3.68 (s, 1H), 4.99 (s, 2H), 6.25 (d, 1H), 6.55 (s, 2H), 6.80–7.96 (m, 3H), 7.20–7.43 (m, 6H), 7.70–7.81 (m, 2H), 8.20 (d, 1H).

EXAMPLE IX (4-{4-(Benzyloxy)-3-[(4-fluorophenyl)sulphonyl]benzyl}-3,5-dimethylphenoxy)(triisopropyl)silane

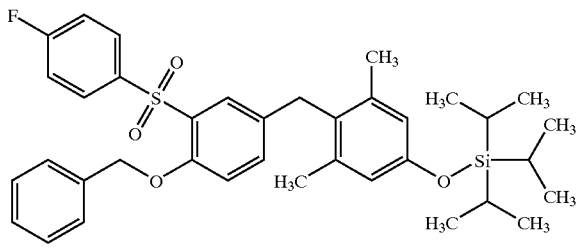

575 mg (0.89 mmol) of {4-(benzyloxy)-3-[(4-fluorophenyl)sulphonyl]phenyl}{2,6-dimethyl-4-[(triisopropylsilyl)oxy]phenyl}methanol (Example VIII) are dissolved in 10 ml of tetrahydrofuran. At 0° C., 1030.35 mg (8.86 mmol) of triethylsilane are initially added, and 78.78 mg (0.35 mmol) of trimethylsilyl trifluoromethanesulphonate are then added dropwise. The reaction mixture is stirred for 1.5 hours, and saturated ammonium chloride solution is then added. The mixture is extracted three times with ethyl acetate, the combined organic phases are dried over sodium sulphate and the solvent is removed under reduced pressure. This gives 611 mg (53% of theory) of (4-{4-(benzyloxy)-3-[(4-fluorophenyl)sulphonyl]benzyl}-3,5-dimethylphenoxy)(triisopropyl)silane.

¹H-NMR (200 MHz, CDCl₃): δ=1.04–1.35 (m, 21H), 2.16 (s, 6H), 3.97 (s, 2H), 4.94 (s, 2H), 6.60 (s, 2H), 6.73–7.1 (m, 4H), 7.2–7.43 (m, 5H), 7.71–7.80 (m, 2H), 7.96 (d, 1H).

EXAMPLE X

4-{4-(Benzyloxy)-3-[(4-fluorophenyl)sulphonyl]benzyl}-3,5-dimethylphenol

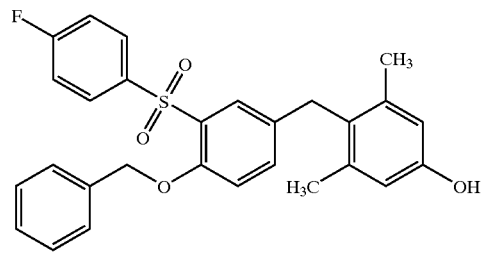

600 mg (9.95 mmol) of (4-{4-(benzyloxy)-3-[(4-fluorophenyl)sulphonyl]benzyl}-3,5-dimethylphenoxy)-(triisopropyl)silane (Example IX) are dissolved in 15 ml of dichloroethane. At room temperature, 359 mg (1.14 mmol) of tetrabutylammonium fluoride are added, and the mixture is stirred for thirty minutes. The solvent is then removed under reduced pressure and the product is purified by silica gel chromatography (mobile phase cyclohexane/ethyl acetate 9:1). This gives 180 mg (40% of theory) of 4-{4-(benzyloxy)-3-[(4-fluorophenyl)sulphonyl]benzyl}-3,5-dimethylphenol.

¹H-NMR (200 MHz, CDCl₃): δ=2.18 (s, 6H), 3.97 (s, 2H), 4.48 (s, 1H), 4.95 (s 2H), 6.57 (s, 2H), 7.02–7.04 (m, 4H), 7.20–7.40 (m, 5H), 7.70–7.82 (m, 2H), 7.95 (d, 1H).

EXAMPLE XI

Ethyl(4-{4-(benzyloxy)-3-[(4-fluorophenyl)sulphonyl]benzyl}-3,5-dimethylphenoxy)acetate

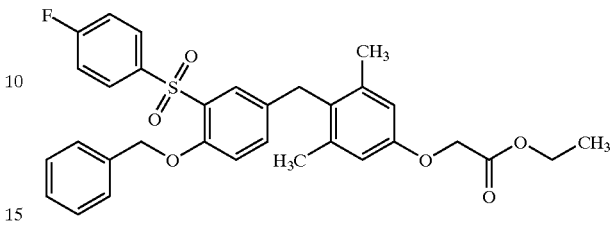

85 mg (0.18 mmol) of 4-{4-(benzyloxy)-3-[(4-fluorophenyl)sulphonyl]benzyl}-3,5-dimethylphenol (Example X) are dissolved in 2 ml of dimethylformamide. 30 mg (0.21 mmol) of potassium carbonate and 33 mg (0.20 mmol) of bromoethyl acetate are added. The mixture is stirred at room temperature overnight. Saturated ammonium chloride solution is then added, and the mixture is extracted three times with diethyl ether. The combined organic phases are washed three times with water, dried with sodium sulphate and concentrated under reduced pressure. This gives 80 mg (96.5% of theory) of ethyl (4-{4-(benzyloxy)-3-[(4-fluorophenyl)sulphonyl]benzyl}-3,5-dimethylphenoxy)acetate.

¹H-NMR (200 MHz, CDCl₃): δ=1.31 (t, 3H), 2.19 (s, 6H), 3.98 (s, 2H), 4.27 (q, 2H), 4.61 (s, 2H), 4.95 (s, 2H), 6.64 (s, 2H), 6.72–7.10 (m, 4H), 7.20–7.39 (m, 5H), 7.71–7.82 (m, 2H), 7.96 (d, 1H).

EXAMPLE XII

Ethyl 2-(4-{4-(benzyloxy)-3-[(4-fluorophenyl)sulphonyl]benzyl}-3,5-dimethylphenoxy)-2-methylpropanoate

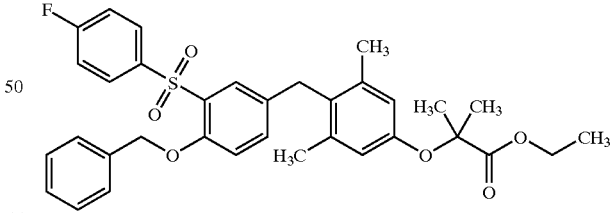

This compound was obtained analogously to Example XI starting from 4-{4-(benzyloxy)-3-[(4-fluorophenyl)sulphonyl]benzyl}-3,5-dimethylphenol (Example X) and ethyl dimethylbromoacetate.

¹H-NMR (200 MHz, CDCl₃): δ=1.27 (t, 3H), 1.56 (s, 3H), 1.60 (s, 3H), 2.16 (s, 6H), 3.97 (s, 2H), 4.26 (q, 2H), 4.95 (s, 2H), 6.57 (s, 2H), 6.73–7.01 (m, 4H), 7.20–7.39 (m, 5H), 7.73–7.80 (m, 2H), 7.96 (d, 1H).

EXAMPLE XIII

4-{3-[(4-Fluorophenyl)sulphonyl]-4-hydroxyphenoxy}-3,5-bis(trifluoromethyl)benzaldehyde

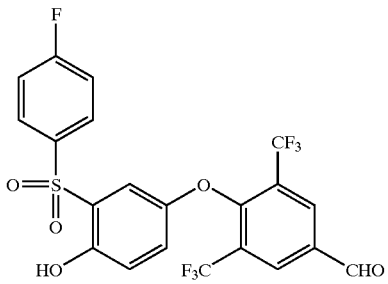

3.42 g (12.75 mmol) of 2-[(4-fluorophenyl)sulphonyl]-1,4-benzenediol [prepared according to WO 00/58279] are dissolved in 150 ml of DMSO, 1.94 g (14.02 mmol) of solid potassium carbonate are added, the mixture is stirred at room temperature for 10 minutes, and 3.53 g (12.75 mmol) of 3,5-bis(trifluoromethyl)-4-chlorobenzaldehyde [prepared analogously to McBee et al., J. Amer. Chem. Soc. 72 4053 (1950)] are introduced a little at a time. After four hours at 50° C., the reaction solution is poured into a mixture of ethyl acetate/ammonium chloride solution. Following phase separation, the aqueous phase is reextracted with ethyl acetate and the combined organic phases are washed twice with sodium chloride solution and dried over sodium sulphate. Filtration and removal of the solvent by distillation is followed by chromatography of the crude product on silica gel 60 using the mobile phase toluene/ethyl acetate 5:1.

Yield: 5.79 g (89.3% of theory)

$R_f$=0.28 (toluene/ethyl acetate 9:1)

MS (ES): m/z=509 [M+H]$^+$ $^1$H-NMR (300 MHz, CDCl$_3$): δ=7.00 (m, 3H), 7.22 (t, 2H), 7.85 (m, 2H), 8.45 (s, 2H), 8.72 (s, 1H), 10.12 (s, 1H).

EXAMPLE XIV

4-[4-Hydroxy-3-(phenylsulphonyl)phenoxy]-3,5-bis(trifluoromethyl)benzaldehyde

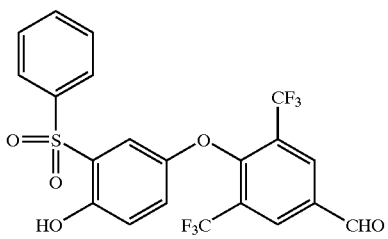

Analogously to Example XIII, 0.5 g (2.0 mmol) of 2-phenylsulphonyl-1,4-hydroquinone is reacted with 0.55 g (2.0 mmol) of 3,5-bis(trifluoromethyl)-4-chlorobenzaldehyde in the presence of 0.3 g (2.2 mmol) of potassium carbonate in 25 ml of DMSO at 50° C. The product is purified by chromatography on silica gel 60 using the mobile phase toluene/ethyl acetate 5:1.

Yield: 0.73 g (72.7% of theory)

$R_f$=0.35 (toluene/ethyl acetate 9:1)

MS (DCI): m/z=508 [M+NH$_4$]$^+$ $^1$H-NMR (300 MHz, CDCl$_3$): δ=7.00 (m, 3H), 7.53 (t, 2H), 7.63 (t, 1H), 7.73 (d, 2H), 8.45 (s, 2H), 8.81 (s, 1H), 10.12 (s, 1H).

EXAMPLE XV 3,5-Dichloro-4-[4-hydroxy-3-(phenylsulphonyl)phenoxy]benzaldehyde

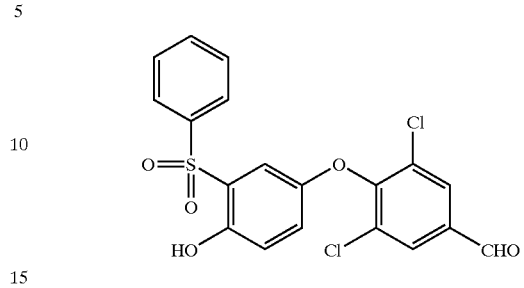

Analogously to Example XIII, 4.18 g (16.71 mmol) of 2-phenylsulphonyl-1,4-hydroquinone are reacted at 60° C. overnight with 3.5 g (16.71 mmol) of 4,5,6-trichlorobenzaldehyde [lit.: van de Bunt, Recl. Trav. Chim. Pays-Bas 48, 131 (1929)] in the presence of 2.54 g (18.38 mmol) of potassium carbonate in 170 ml of DMSO. The product is purified by chromatography on silica gel 60 using the mobile phase toluene/ethyl acetate 5:1.

Yield: 4.78 g (67.6% of theory)

$R_f$=0.30 (toluene/ethyl acetate 9:1)

MS (DCI): m/z=440 [M+NH$_4$]$^+$ $^1$H-NMR (200 MHz, CDCl$_3$): δ=7.00 (m, 2H), 7.10 (d, 1H), 7.60 (m, 3H), 7.90 (m, 4H), 8.87 (s, 1H), 9.94 (s, 1H).

Preparation Examples

Example 1

Ethyl (4-{3-[(4-fluorophenyl)sulphonyl]-4-hydroxybenzyl}-3,5-dimethylphenoxy)acetate

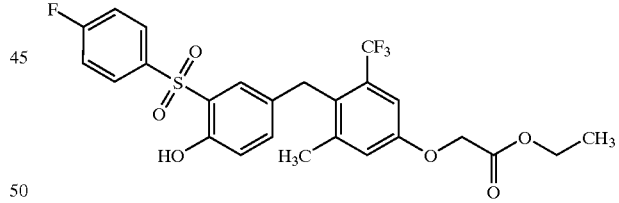

50 mg (0.09 mmol) of ethyl (4-{4-(benzyloxy)-3-[(4-fluorophenyl)sulphonyl]benzyl}-3,5-dimethylphenoxy)acetate (Example XI) are dissolved in 20 ml of ethanol. 10 mg of palladium on activated carbon (10%) are added, and the mixture is hydrogenated at 1013 mbar and room temperature for 2 hours. The reaction mixture is then filtered through Celite and the solvent is removed under reduced pressure. This gives 37 mg (86% of theory) of ethyl (4-{3-[(4-fluorophenyl)sulphonyl]-4-hydroxybenzyl}-3,5-dimethylphenoxy)acetate.

$^1$H-NMR (200 MHz, CDCl$_3$): δ=1.31 (t, 3H), 2.10 (s, 6H), 3.86 (s, 2H), 4.29 (q, 2H), 4.61 (s, 2H), 6.61 (s, 2H), 6.86 (m, 1H), 6.98–7.05 (m, 1H), 7.16–7.23 (m, 3H), 7.84–7.90 (m, 2H), 8.94 (s, 1H).

Example 2

(4-{3-[(4-Fluorophenyl)sulphonyl]-4-hydroxybenzyl}-3,5-dimethylphenoxy)acetic acid

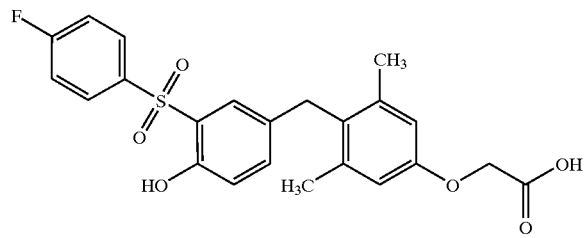

37 mg (0.08 mmol) of ethyl (4-{3-[(4-fluorophenyl)sulphonyl]-4-hydroxybenzyl}-3,5-dimethylphenoxy)acetate (Example 1) are dissolved in 1 ml of ethanol, and a few drops of 1 N aqueous sodium hydroxide solution are added. The mixture is stirred at room temperature for thirty minutes and the solvent is then removed under reduced pressure. Water is added to the residue, and the mixture is extracted three times with ethyl acetate. The combined organic phases are dried with sodium sulphate and concentrated. This gives 32 mg (90% of theory) of (4-{3-[(4-fluorophenyl)sulphonyl]-4-hydroxybenzyl}-3,5-dimethylphenoxy)acetic acid.

$^1$H-NMR (200 MHz, CDCl$_3$): δ=2.13 (s, 6H), 3.87 (s, 2H), 4.67 (s, 2H), 6.64 (s, 2H), 6.72–7.28 (m, 5H), 7.77–7.92 (m, 2H), 8.94 (s, 1H).

Example 3

2-(4-{3-[(4-Fluorophenyl)sulphonyl]-4-hydroxybenzyl}-3,5-dimethylphenoxy)-2-methylpropionic acid

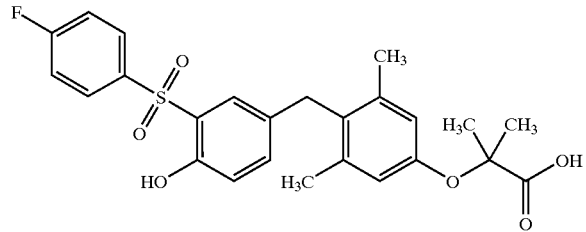

This compound was obtained analogously to Examples 1 and 2 starting from ethyl 2-(4-{4-(benzyloxy)-3-[(4-fluorophenyl)sulphonyl]benzyl}-3,5-dimethylphenoxy)-2-methylpropanoate (Example XII).

$^1$H-NMR (200 MHz, CDCl$_3$): δ=1.60 (s, 6H), 2.11 (s, 6H), 3.88 (s, 2H), 6.66 (s, 2H), 6.85–7.30 (m, 5H), 7.84–7.91 (m, 2H), 8.94 (broad s, 1H).

Example 4

Ethyl (2E)-3-[4-{3-[(4-fluorophenyl)sulphonyl]-4-hydroxyphenoxy}-3,5-bis(trifluoromethyl)phenyl]-2-propenoate

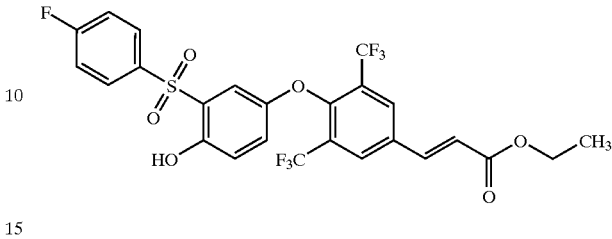

Under argon, 0.5 g (0.98 mmol) of the aldehyde from Example XII is dissolved in (15 ml of toluene, and 0.38 g (1.08 mmol) of ethoxycarbonylmethylenetriphenylphosphorane is added a little at a time. After four days of stirring at room temperature, the reaction mixture is concentrated to half of its original volume and chromatographed on silica gel 60 using the mobile phase toluene/ethyl acetate 9:1.

Yield: 0.564 g (96.5% of theory)

R$_f$=0.35 (toluene/ethyl acetate 9:1)

MS (ESI): m/z=579 [M+H]$^+$ $^1$H-NMR (300 MHz, CDCl$_3$): δ=1.36 (t, 3H), 4.30 (q, 2H), 6.55 (d, 1H), 6.96 (m, 3H), 7.70 (d, 1H), 7.85 (q, 3H), 8.05 (s, 2H), 8.18 (s, 1H), 8.68 (s, 1H).

Example 5

(2E)-3-[4-{3-[(4-Fluorophenyl)sulphonyl]-4-hydroxyphenoxy}-3,5-bis(trifluoromethyl)phenyl]-2-propenoic acid

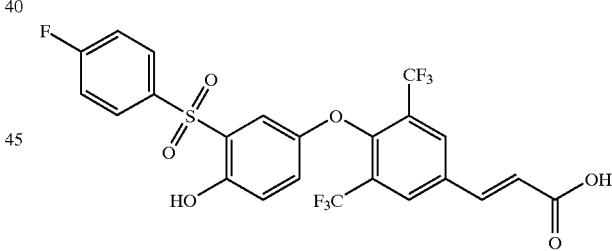

0.53 g (0.92 mmol) of the cinnamic ester from Example 4 is dissolved in 15 ml of dioxane, 8 ml of 1 M aqueous sodium hydroxide solution are added and the mixture is stirred at room temperature for one hour. The solution is acidified to pH 4 using 1 N hydrochloric acid and extracted twice with ethyl acetate, and the combined organic phases are then washed with sodium chloride solution, dried over sodium sulphate, filtered, concentrated completely and dried under high vacuum.

Yield: 0.53 g (quant.)

R$_f$=0.22 (toluene/ethyl acetate 1:1)

MS (ESI): m/z=573 [M+Na]$^+$ $^1$H-NMR (200 MHz, CDCl$_3$): δ=6.58 (d, 1H), 7.00 (m, 4H), 7.18 (m, 2H), 7.83 (m, 3H), 8.08 (s, 2H), 8.20 (s, 1H).

Example 6

3-[4-{3-[(4-Fluorophenyl)sulphonyl]-4-hydroxyphenoxy}-3,5-bis(trifluoromethyl)-phenyl]propionic acid

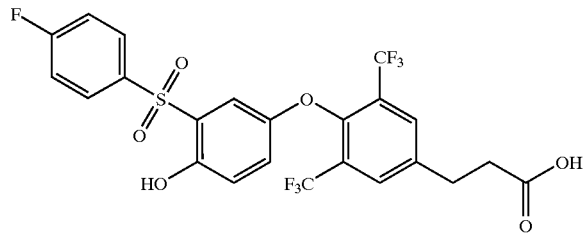

0.5 g (0.91 mmol) of the cinnamic acid from Example 5 is dissolved in 100 ml of methanol, 200 mg of palladium on activated carbon (10%) is added and the mixture is hydrogenated overnight at a hydrogen pressure of 3 bar. The hydrogenation solution is filtered off with suction through kieselguhr, the filtrate is concentrated and the residue is chromatographed on silica gel 60 using the mobile phase toluene/ethyl acetate 1:1.

Yield: 49 mg (9.2% of theory)

$R_f$=0.27 (toluene/ethyl acetate 1:1)

MS (ESI): m/z=575 [M+Na]$^+$ $^1$H-NMR (400 MHz, CDCl$_3$): δ=2.80 (t, 2H), 3.10 (t, 2H), 6.91 (m, 2H), 7.02 (dd, 1H), 7.18 (t, 3H), 7.78 (s, 2H), 7.85 (m, 2H), 8.65 (s, 1H).

Example 7

Ethyl (2E)-3-[4-[4-hydroxy-3-(phenylsulphonyl)phenoxy]-3,5-bis(trifluoromethyl)-phenyl]-2-propenoate

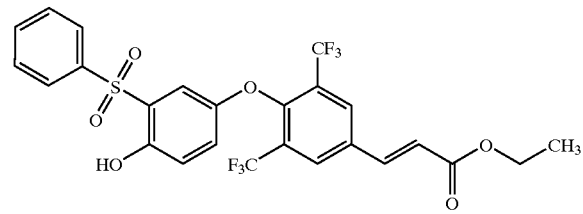

Analogously to the procedure of Example 4, 0.5 g (1.02 mmol) of the aldehyde from Example XIV is stirred at room temperature with 0.39 g (1.12 mmol) of ethoxycarbonylmethylenetriphenylphosphorane in 10 ml of toluene for two days. The crude product is purified by column chromatography on silica gel 60 using the mobile phase toluene/ethyl acetate 9:1.

Yield: 0.55 g (95% of theory)

$R_f$=0.38 (toluene/ethyl acetate 9:1)

MS (DCI):m/z=578 [M+NH$_4$]$^+$ $^1$H-NMR (300 MHz, CDCl$_3$): δ=1.36 (t, 3H), 4.30 (q, 2H), 6.55 (d, 1H), 6.95 (m, 3H), 7.50 (m, 2H), 7.70 (d, 1H), 7.82 (m, 2H), 8.03 (s, 2H), 8.18 (s, 1H), 8.77 (s, 1H).

Example 8

(2E)-3-[4-[4-Hydroxy-3-(phenylsulphonyl)phenoxy]-3,5-bis(trifluoromethyl)phenyl]-2-propenoic acid

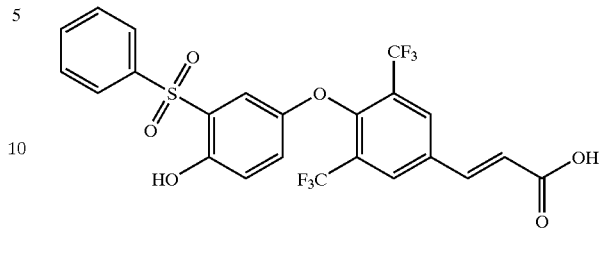

Analogously to the procedure of Example 5, 0.52 g (0.92 mmol) of the cinnamic ester from Example 7 in 15 ml of dioxane is hydrolyzed within two hours using 8 ml of 1 M aqueous sodium hydroxide solution.

Yield: 0.55 g (quant.)

$R_f$=0.18 (toluene/ethyl acetate 1:1)

MS (DCI): m/z=550 [M+NH]$^+$ $^1$H-NMR (200 MHz, CDCl$_3$): δ=6.57 (d, 1H), 6.98 (m, 3H), 7.54 (m, 3H), 7.83 (d 2H), 8.08 (s, 2H), 8.20 (s, 1H).

Example 9

3-[4-[4-Hydroxy-3-(phenylsulphonyl)phenoxy]-3,5-bis(trifluoromethyl)phenyl]-propionic acid

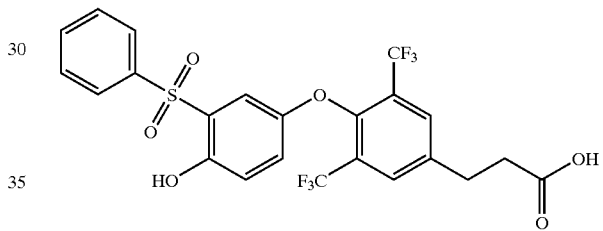

Analogously to the procedure of Example 6, 0.5 g (0.93 mmol) of the cinnamic acid from Example 8 is hydrogenated overnight using palladium on activated carbon (10%) in 100 ml of methanol. The crude product is chromatographed on silica gel 60 using the mobile phase toluenelethyl acetate 1:1.

Yield: 0.345 g (67.8% of theory)

$R_f$=0.22 (toluenelethyl acetate 1:1)

MS (DCI): m/z=552 [M+NH]$^+$ $^1$H-NMR (300 MHz, CDCl$_3$): δ=2.80 (t, 2H), 3.10 (t, 2H), 6.92 (m, 3H), 7.00 (m, 1H), 7.50 (t, 2H), 7.60 (m, 1H), 7.78 (s, 2H), 7.82 (d, 2H), 8.61 (s, 1H).

Example 10

Ethyl (2E)-3-{3,5-dichloro-4-[4-hydroxy-3-(phenylsulphonyl)phenoxy]phenyl}-2-propenoate

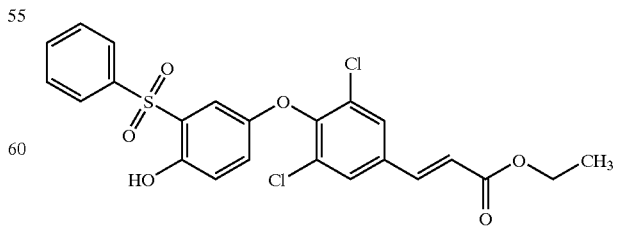

Analogously to the procedure of Example 4, 0.5 g (1.18 mmol) of the aldehyde from Example XV and 0.45 g (1.30 mmol) of ethoxycarbonylmethylenetriphenylphosphorane are stirred in 10 ml of toluene at room temperature for two days. The crude product is purified by column chromatography on silica gel 60 using the mobile phase toluene/ethyl acetate 9:1.

Yield: 0.59 g (96.3% of theory)
$R_f$=0.31 (toluene/ethyl acetate 9:1)
HPLC: $R_t$=5.03 min (Kromasil column C18, 60×2 mm; 0.5% $HClO_4$/acetonitrile, flow rate 0.75 ml/min; 210 nm)
MS (DCI): m/z=510 $[M+NH_4]^+$
$^1$H-NMR (300 MHz, $CDCl_3$): δ=1.35 (t, 3H), 4.28 (q, 2H), 6.41 (d, 1H), 6.98 (m 2H), 7.11 (m, 1H), 7.50–7.66 (m, 6H), 7.90 (d, 2H), 8.82 (s, 1H).

Example 11
(2E)-3-{3,5-Dichloro-4-[4-hydroxy-3-(phenylsulphonyl) phenoxy]phenyl}-2-propenoic acid

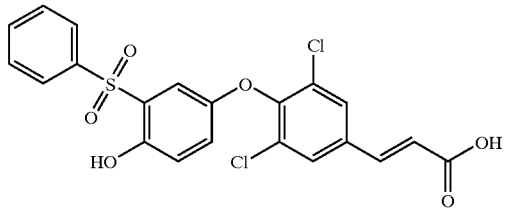

Analogously to the procedure of Example 5, 0.57 g (1.16 mmol) of the cinnamic ester from Example 10 in 15 ml of dioxane is hydrolyzed at room temperature within two hours using 8 ml of 1 M aqueous sodium hydroxide solution.

Yield: 0.62 g (quant.)
$R_f$=0.18 (toluene/ethyl acetate 1:1)
HPLC: $R_t$=4.47 min (Kromasil column C18, 60×2 mm; 0.5% $HClO_4$/acetonitrile, flow rate 0.75 ml/min; 210 nm)
MS (ESI): m/z=487 $[M+Na]^+$
$^1$H-NMR (400 MHz, DMSO-$d_6$): δ=6.75 (d, 1H), 6.90 (d, 1H), 7.11 (m, 1H), 7.26 (m, 1H), 7.60 (t, 3H), 7.70 (t, 1H), 7.88 (d, 2H), 7.96 (s, 1H), 8.10 (s, 1H) 10.70 (s, 1H), 12.64 (s, 1H).

The examples below are prepared analogously to the processes given above:

Example 12
(4-{3-[(4-Fluorophenyl)sulphonyl]-4-hydroxyphenoxy}-3,5-dimethylphenoxy)acetic acid Example 13
2-(4-{3-[(4-Fluorophenyl)sulphonyl]-4-hydroxyphenoxy}-3,5-dimethylphenoxy)-2-methylpropionic acid Example 14
3-(4-{3-[(4-Fluorophenyl)sulphonyl]-4-hydroxyphenoxy}-3,5-dimethylphenoxy)propionic acid Example 15
[(4-{3-[(4-Fluorophenyl)sulphonyl]-4-hydroxybenzyl}-3,5-dimethylphenyl)-sulphanyl]acetic acid Example 16
(4-{3-[(4-Fluorophenyl)sulphonyl]-4-hydroxybenzyl}-3,5-dimethylphenyl)acetic acid Example 17
Fluoro-(4-{3-[(4-fluorophenyl)sulphonyl]-4-hydroxybenzyl}-3,5-dimethylphenyl)acetic acid Example 18
(4-{3-[(4-Fluorophenyl)sulphonyl]-4-hydroxyphenoxy}-3,5-dimethylphenyl)acetic acid Example 19
[(4-{3-[(4-Fluorophenyl)sulphonyl]-4-hydroxyphenoxy}-3,5-dimethylphenyl)-sulphanyl]acetic acid Example 20
Fluoro-(4-{3-[(4-fluorophenyl)sulphonyl]-4-hydroxyphenoxy}-3,5-dimethylphenyl)acetic acid Example 21
(3,5-Dichloro4-{3-[(4-fluorophenyl)sulphonyl]-4-hydroxyphenoxy}phenyl)acetic acid Example 22
(3,5-Dibromo-4-{3-[(4-fluorophenyl)sulphonyl]-4-hydroxyphenoxy}phenyl)acetic acid Example 23
[3-Chloro4-{3-[(4-fluorophenyl)sulphonyl]-4-hydroxyphenoxy}-5-(trifluoromethyl)phenyl]acetic acid Example 24
[4-{3-[(4-Fluorophenyl)sulphonyl]-4-hydroxyphenoxy}-3,5-bis(trifluoromethyl)-phenyl]acetic acid Example 25
3-[3-Chloro-4-{3-[(4-fluorophenyl)sulphonyl]-4-hydroxyphenoxy}-5-(trifluoromethyl)phenyl]propionic acid Example 26
3-(3,5-Dichloro-4-{3-[(4-fluorophenyl)sulphonyl]-4-hydroxyphenoxy}phenyl)propionic acid Example 27
3-{3,5-Dichloro-4-[4-hydroxy-3-(phenylsulphonyl) phenoxy]phenyl}propionic acid Example 28
3-(3,5-Dibromo-4-{3-[(4-fluorophenyl)sulphonyl]-4-hydroxyphenoxy}phenyl)propionic acid

What is claimed is:
1. A compound of the formula (I)

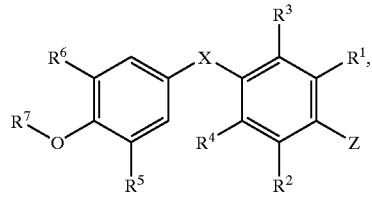

in which
X represents O, S, SO, $SO_2$, $CH_2$, CHF, $CF_2$ or represents $NR^8$ in which $R^8$ represents hydrogen or ($C_1$–$C_4$)-alkyl,
$R^1$ and $R^2$ are identical or different and represent hydrogen or ($C_1$–$C_4$)-alkyl,
$R^3$ and $R^4$ are identical or different and represent hydrogen, halogen, cyano, ($C_1$–$C_6$)-alkyl, $CF_3$, $CHF_2$, $CH_2F$, vinyl or ($C_3$–$C_7$)-cycloalkyl, where at least one of the two substituents is not hydrogen,
$R^5$ represents hydrogen, ($C_1$–$C_4$)-alkyl or halogen,
$R^6$ represents a group of the formula —S—$R^9$, —S(O)$_n$—$R^{10}$ or —$NR^{11}$—C(O)—$R^{12}$, in which
$R^9$ represents phenyl or benzyl where the abovementioned radicals are optionally substituted by one, two or three identical or different substituents selected from the group consisting of halogen, hydroxyl, oxo, cyano, $(C_1-C_6)$-alkyl, $(C_1-C_6)$-alkoxy, carboxyl and $(C_1-C_4)$-alkoxycarbonyl, n represents the number 1 or 2, $R^{10}$ represents phenyl or benzyl, where the abovementioned radicals are optionally substituted by one, two or three identical or different substituents selected from the group consisting of halogen, hydroxyl, oxo, cyano, nitro, amino, $NR^{18}R^{19}$, trifluoromethyl, $(C_1-C_6)$-alkyl, optionally $R^{20}$-substituted $(C_1-C_6)$-alkoxy, $(C_3-C_8)$-cycloalkyl, $(C_6-C_{10})$-aryl, which for its part is optionally substituted by halogen, $(C_1-C_4)$-alkyl, $(C_1-C_4)$-alkoxy, trifluoromethyl, nitro or cyano, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and each represents hydrogen, phenyl, benzyl, $(C_1-C_6)$-alkyl or $(C_3-C_8)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, or by phenyl which for its part is optionally substituted by halogen or hydroxyl, $R^{11}$ represents hydrogen or benzyl where the latter for its part is optionally substituted by halogen, triflouromethyl, $(C_1-C_6)$-alkyl or $(C_1-C_6)$-alkoxy, $R^{12}$ represents benzyl which may be substituted up to three times by identical or different substituents from the group consisting of halogen, $(C_1-C_6)$-alkyl and $(C_1-C_4)$-alkoxy, or represents phenyl which may be substituted up to three times by identical or different substituents from the group consisting of $(C_1-C_6)$-alkyl, $(C_1-C_6)$-alkoxy, halogen, cyano, amino, trifluoromethyl and phenyl, $R^7$ represents hydrogen, $(C_1-C_4)$-alkyl or $(C_1-C_4)$-alkanoyl, and Z represents a group of the formula

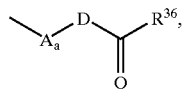

in which

A represents O or S, a represents the number 0 or 1,

D represents a straight-chain $(C_1-C_4)$-alkylene group which may be mono- or polysubstituted by identical or different substituents from the group consisting of $(C_1-C_3)$-alkyl, hydroxyl and fluorine, and $R^{36}$ represents $OR^{37}$ or $NR^{38}R^{39}$, in which $R^{37}$, $R^{38}$ and $R^{39}$ are identical or different and each represents hydrogen, phenyl, benzyl, $(C_1-C_6)$-alkyl or $(C_3-C_8)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, or by phenyl which for its part is optionally substituted by halogen or hydroxyl, or a pharmaceutically acceptable salt, solvate, hydrate, or hydrate of a salt thereof.

2. A compound of the formula (I) according to claim 1 in which

X represents O, S, $CH_2$ or $CF_2$, $R^1$ and $R^2$ are identical or different and represent hydrogen or methyl, $R^3$ and $R^4$ are identical or different and represent hydrogen, halogen, $(C_1-C_4)$-alkyl, $CF_3$, $CHF_2$, $CH_2F$, vinyl or $(C_3-C_5)$-cycloalkyl, where at least one of the two substituents is not hydrogen, $R^5$ represents hydrogen, $(C_1-C_3)$-alkyl, fluorine, chlorine or bromine, $R^6$ represents a group of the formula —$S(O)_2$—$R^{10}$ or —$NR^{11}$—C(O)—$R^{12}$, in which $R^{10}$ represents phenyl or benzyl where the abovementioned radicals are optionally substituted by one, two or three identical or different substituents selected from the group consisting of halogen, hydroxyl, oxo, cyano, nitro, amino, dimethylamino, trifluoromethyl, $(C_1-C_4)$-alkyl, $(C_1-C_4)$-alkoxy, $(C_3-C_6)$-cycloalkyl, or phenyl, which for its parts is optionally substituted by halogen, $(C_1-C_4)$-alkyl, $(C_1-C_4)$-alkoxy, trifluoromethyl, nitro or cyano, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{22}$ $R^{23}$, $R^{24}$, $R^{25}$, $R^{26}$, $R^{27}$ and $R^{28}$ are identical or different and each represents hydrogen, phenyl, benzyl, $(C_1-C_4)$-alkyl or $(C_5-C_7)$-cycloalkyl which for their part are optionally mono- or polysubstituted by identical or different substituents from the group consisting of halogen, hydroxyl, amino, carboxyl, $(C^1-C_4)$-alkoxy, $(C_1-C_4)$-alkoxycarbonyl, $(C_1-C_4)$-alkoxycarbonylamino or $(C_1-C_5)$-alkanoyloxy, $R^{11}$ represents hydrogen or benzyl, $R^{12}$ represents benzyl which may be substituted up to three times by identical or different substituents from the group consisting of halogen, $(C_1-C_4)$-alkyl and $(C_1-C_4)$-alkoxy, or represents phenyl which may be substituted up to three times by identical or different substituents from the group consisting of $(C_1-C_4)$-alkyl, $(C_1-C_4)$-alkoxy, halogen, cyano, amino and trifluoromethyl, $R^7$ represents hydrogen, methyl or acetyl, and Z represents a group of the formula

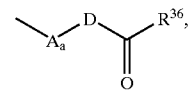

in which

A represents O or S, a represents the number 0 or 1,

D represents a straight-chain $(C_1-C_3)$-alkylene group which may be mono- or polysubstituted by identical or different substituents from the group consisting of methyl, hydroxyl and fluorine, and $R^{36}$ represents $OR^{37}$ or $NR^{38}R^{39}$, in which $R^{37}$ represents hydrogen, phenyl, benzyl, $(C_1-C_6)$-alkyl or $(C_3-C_7)$-cycloalkyl which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, and $(C_1-C_5)$-alkanoyloxy, and $R^{38}$ and $R^{39}$ are identical or different and each represents hydrogen, $(C_1-C_6)$-alkyl or $(C_3-C_7)$-cycloalkyl, which for their part are optionally mono- or polysubstituted by identical or different substituents from the group consisting of halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, and phenyl which for its part is optionally substituted by halogen or hydroxyl, or a pharmaceutically acceptable salt, solvate, hydrate, or hydrate of a salt thereof.

3. A compound of the general formula (I) according to claim 1 in which

X represents O, S or $CH_2$, $R^1$ and $R^2$ represent hydrogen, $R^3$ and $R^4$ are identical or different and represent methyl, ethyl, propyl, isopropyl, cyclopropyl, trifluoromethyl, chlorine or bromine, $R^5$ represents hydrogen, $R^6$ represents a group of the formula $-S(O)_2-R^{10}$, in which $R^{10}$ represents phenyl which is optionally mono- or disubstituted by identical or different substituents from the group consisting of fluorine, chlorine, bromine, hydroxyl, cyano, trifluoromethyl, $(C_1-C_4)$-alkyl, $(C_1-C_4)$-alkoxy, carboxyl and $(C_1-C_4)$-alkoxycarbonyl, $R^7$ represents hydrogen, and Z represents a group of the formula

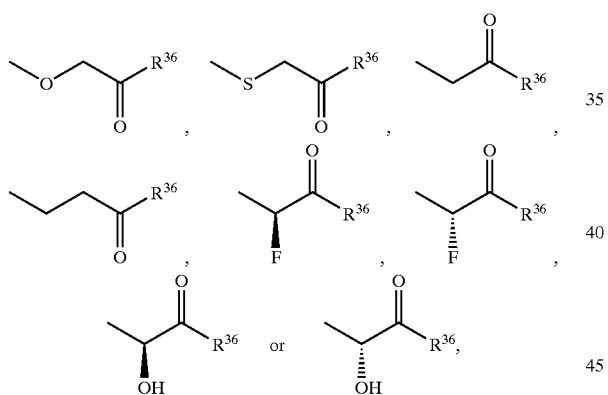

in which $R^{36}$ represents hydroxyl or the radical $-C(O)-R^{36}$ has the meanings of $R^{36}$ given above for a group which, in the sense of a prodrug, can be degraded to the carboxylic acid $-C(O)-OH$ or a salt thereof, or a pharmaceutically acceptable salt, solvate, hydrate, or hydrate of a salt thereof.

4. A compound of the formula (I) according to claim 1 in which

X represents $CH_2$ or oxygen, $R^1$ and $R^2$ represent hydrogen, $R^3$ and $R^4$ are identical or different and represent methyl, ethyl, propyl, isopropyl, cyclopropyl, trifluoromethyl, chlorine or bromine, $R^5$ represents hydrogen, $R^6$ represents a group of the formula $-S(O)_2-R^{10}$, in which $R^{10}$ represents phenyl, which is optionally mono- or disubstituted by identical or different substituents from the group consisting of fluorine, chlorine, bromine, hydroxyl, cyano, trifluoromethyl, $(C_1-C_4)$-alkyl, $(C_1-C_4)$-alkoxy, carboxyl and $(C_1-C_4)$-alkoxycarbonyl, $R^7$ represents hydrogen, and Z represents a group of the formula

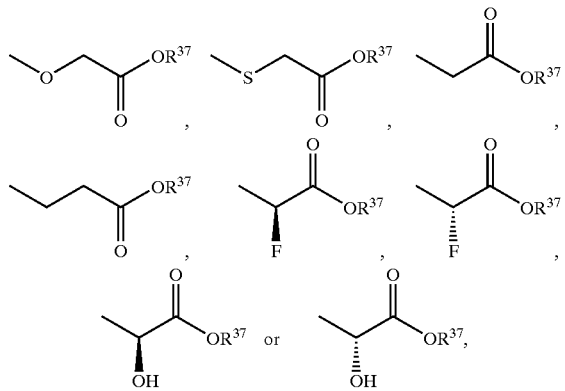

in which $R^{37}$ represents hydrogen, $(C_1-C_4)$-alkyl or $(C_4-C_6)$-cycloalkyl, or a pharmaceutically acceptable salt, solvate, hydrate, or hydrate of a salt thereof.

5. A compound of the formula (Ia)

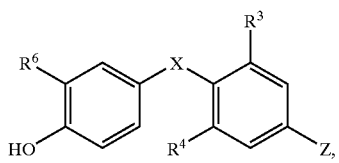

(Ia)

in which

X represents $CH_2$ or O, $R^3$ and $R^4$ are identical or different and represent bromine, trifluoromethyl, ethyl, cyclopropyl, methyl or chlorine, Z represents a group of the formula $-CH_2-C(O)-OH$, $-CH_2-CH_2-C(O)-OH$, $-O-CH_2-C(O)-OH$ or $-S-CH_2-C(O)-OH$, and $R^6$ represents a group of the formula $-S(O)_2-R^{10}$, in which $R^{10}$ represents phenyl which is optionally mono- or disubstituted by identical or different substituents from the group consisting of fluorine, chlorine, cyano, trifluoromethyl, methyl, hydroxyl and methoxy.

6. A compound of the formula (Ia)

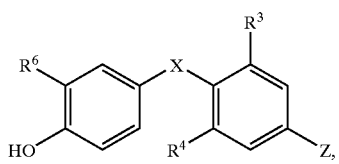

(Ia)

in which

X represents $CH_2$ or O, $R^3$ and $R^4$ are identical or different and represent bromine, trifluoromethyl, ethyl, cyclopropyl, methyl or chlorine, Z represents a group of the formula —CH$_2$—C(O)—OH, —CH$_2$—CH$_2$—C(O)—OH, —O—CH$_2$—C(O)—OH, —O—C[(CH$_3$)$_2$]—C(O)—OH or —S—CH$_2$—C(O)—OH, and R$^6$ represents a group of the formula —S(O)$_2$—R$^{10}$, in which R$^{10}$ represents phenyl which is optionally mono- or disubstituted by identical or different substituents from the group consisting of fluorine, chlorine, cyano, trifluoromethyl, methyl, hydroxyl and methoxy.

7. A pharmaceutical composition comprising at least one compound of the formula (I) as defined in any one of claims 1 to 6.

8. A process for preparing pharmaceutical composition, characterized in that at least one compound of the formula (I) as defined in any one of claims 1 to 6 is converted, using excipients or carriers, into a suitable administration form.

9. A method of treating arteriosclerosis, obesity or hypercholesterolaemia comprising administering to a host in need thereof an effective amount of a composition of claim 7.

10. A method of treating depression, goiter or cancer of the thyroid gland comprising administering to a host in need thereof an effective amount of a composition of claims 7.

11. A method for the treatment of arteriosclerosis, hypercholesterolaemia, dyslipidaemia, obesity, cardiac insufficiency, pulmonary emphysema, pain, migraine, osteoporosis, cardiac arrhythmias, hypothyroidism, or diabetes comprising administering to a host in need thereof an effective amount of a compound as defined in any one of claims 1 to 6.

12. A process for preparing compounds of the formula (I) as defined in claim 1, characterized in that a reactive phenol derivative of the formula (II)

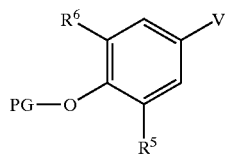

(II)

in which
R$^5$ and R$^6$ are as defined in claim 1 and
PG represents a protective group and
V represents a binding or leaving group,
is reacted, if appropriate with isolation of the intermediates, or directly, with a reactive phenyl derivative of the formula (III)

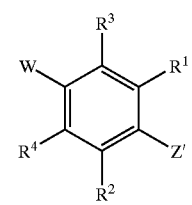

(III)

in which
R$^1$, R$^2$, R$^3$ and R$^4$ are as defined in claim 1 and
W represents a binding or leaving group and
Z' has the meaning given for Z or represents OH, O—PG, SH, S—PG, or represents an aldehyde, cyano, carboxyl or (C$_1$–C$_4$)-alkoxycarbonyl group,
if appropriate in the presence of inert solvent and a catalyst, to give a compound of the formula (I).

* * * * *